US012806242B2

(12) United States Patent
Lu et al.

(10) Patent No.: US 12,806,242 B2
(45) Date of Patent: Nov. 24, 2026

(54) POLYPEPTIDE, AND PREPARATION METHOD THEREFOR AND USE THEREOF

(71) Applicant: SHANXI JINBO BIO-PHARMACEUTICAL CO., LTD., Taiyuan (CN)

(72) Inventors: Lu Lu, Shanghai (CN); Shibo Jiang, Shanghai (CN); Shuai Xia, Shanghai (CN); Xia Yang, Shanghai (CN)

(73) Assignee: SHANXI JINBO BIO-PHARMACEUTICAL CO., LTD., Taiyuan (CN)

( * ) Notice: Subject to any disclaimer, the term of this patent is extended or adjusted under 35 U.S.C. 154(b) by 918 days.

(21) Appl. No.: 17/777,567

(22) PCT Filed: Jan. 11, 2021

(86) PCT No.: PCT/CN2021/071078
§ 371 (c)(1),
(2) Date: May 17, 2022

(87) PCT Pub. No.: WO2021/155733
PCT Pub. Date: Aug. 12, 2021

(65) Prior Publication Data

US 2022/0409694 A1 Dec. 29, 2022

(30) Foreign Application Priority Data

Feb. 5, 2020 (CN) ......................... 202010080751.4

(51) Int. Cl.

| | |
|---|---|
| ***A61K 38/16*** | (2006.01) |
| ***A61K 31/4045*** | (2006.01) |
| ***A61K 31/427*** | (2006.01) |
| ***A61K 31/4706*** | (2006.01) |
| ***A61K 31/472*** | (2006.01) |
| ***A61K 31/4965*** | (2006.01) |
| ***A61K 31/513*** | (2006.01) |
| ***A61K 31/635*** | (2006.01) |
| ***A61K 31/706*** | (2006.01) |
| ***A61P 31/14*** | (2006.01) |
| ***C07K 14/00*** | (2006.01) |

(52) U.S. Cl.
CPC ........ *A61K 38/162* (2013.01); *A61K 31/4045* (2013.01); *A61K 31/427* (2013.01); *A61K 31/4706* (2013.01); *A61K 31/472* (2013.01); *A61K 31/4965* (2013.01); *A61K 31/513* (2013.01); *A61K 31/635* (2013.01); *A61K 31/706* (2013.01); *A61P 31/14* (2018.01); *C07K 14/00* (2013.01)

(58) Field of Classification Search
None
See application file for complete search history.

(56) References Cited

U.S. PATENT DOCUMENTS 5,444,044 A 8/1995 Jiang et al.

FOREIGN PATENT DOCUMENTS

| | | | |
|---|---|---|---|
| CN | 106749558 | A | 5/2017 |
| CN | 107022008 | A | 8/2017 |
| WO | WO 2005007671 | A2 | 1/2005 |
| WO | WO 2005063801 | A2 | 7/2005 |
| WO | WO 2005077103 | A2 | 8/2005 |
| WO | WO 2018176103 | A1 | 10/2018 |

OTHER PUBLICATIONS

Xia et al., Cell Res. 30:343-355 (Mar. 30, 2020) (Year: 2020).*
English language machine translation of CN 107022008A obtained for espacenet.com, 9 pages (2017) (Year: 2017).*
Mathieu et al., J. Infect. Dis. 218:218-227 (2018) (Year: 2018).*
Povoski et al., Expert Rev. Mol. Diagn. 13:315-319 (2013) (Year: 2013).*
Xia et al., "Fusion mechanism of 2019-nCOV and fusion inhibitors targeting HR1 domain in spike protein", Cellular & Molecular Immunology, 2020, pp. 765-767.
Xia et al., "A pan-coronavirus fusion inhibitors targeting the HR1 Domain of human coronavirus spike", Science Advances, 5, Apr. 10, 2019, 16 pages.
Lu et al. "Outbreak of pneumonia of unknown etiology in Wuhan, China: The mystery and the miracle" Journal of Medical Virology, 2020, pp. 401-402.
Needleman et al., "A General Method Applicable to the Search for Similarities in the Amino Acid Sequence of Two Proteins", Journal Molecular Biology, 48, 1970, pp. 443-453.
Rice et al., "EMBOSS: The European Molecular Biology Open Software Suite", TIG, vol. 16, No. 6, Jun. 2000, pp. 276-277.
Lu et al., "Structure-based discovery of Middle East respiratory syndrome coronavirus fusion inhibitor", Nature Communications, 5, Jan. 28, 2014, 37 pages.
Wang, C. et al. "Artificial peptides conjugated with cholesterol and pocket-specific small molecules potently inhibit infection by laboratory-adapted and primary HIV-1 isolates and enfuvirtide-resistant HIV-1 strains" J Antimicrob Chemother 2014; 69: 1537-1545; Feb. 4, 2014.
Chong, H. et al. "Development of potent and long-acting HIV-1 fusion inhibitors" AIDS 2016, 30:1187-1196; May 2016.

(Continued)

*Primary Examiner* — Thea D' Ambrosio
(74) *Attorney, Agent, or Firm* — Cozen O'Connor

(57) ABSTRACT

Provided is a polypeptide containing the amino acid sequence as shown in SEQ ID NO. 1, and the present invention belongs to the field of biomedicine. The polypeptide can inhibit the infection with novel coronavirus 2019-nCoV (SARS-CoV-2) and SARS-like viruses, and can thus provide good candidate drugs for the prevention and treatment of 2019-nCoV and SARS-like viruses which may break out in the future. Further provided is a polypeptide derivative having palmic acid or cholesterol modifications.

7 Claims, 7 Drawing Sheets

Specification includes a Sequence Listing.

(56) References Cited

OTHER PUBLICATIONS

Park, J-E et al. "Lipidation increases antiviral activities of coronavirus fusion-inhibiting peptides" Virology 511 (2017) pp. 9-18.
Ingallinella, P et al. "Addition of a cholesterol group to an HIV-1 peptide fusion inhibitor dramatically increases its antiviral potency" PNAS, Apr. 7, 2009, vol. 106, No. 14, pp. 5801-5806.
Xia, S. et al. "Inhibition of SARS-COV-2 (previously 2019-nCOV) infection by a highly potent pan-coronavirus fusion inhibitor targeting its spike protein that harbors a high capacity to mediate membrane fusion" Cell Research, (2020) 30: pp. 343-355.
Xia S. et al. "Peptide-based membrane fusion inhibitors targeting HCoV-229E spike protein HR1 and HR2 domains" International Journal of Molecular Sciences, (2018) 19(2), 487, 15 pages.
Sun Y. et al. "Identification of a novel inhibitor against Middle East respiratory syndrome coronavirus" Viruses (2017) 9(9), 255, 12 pages.
Indian Patent Application No. 202227037890 Examination Report dated May 6, 2026, 9 pages.

* cited by examiner

SEQUENCE LISTING

```
<160> NUMBER OF SEQ ID NOS: 14

<210> SEQ ID NO 1
<211> LENGTH: 36
<212> TYPE: PRT
<213> ORGANISM: Artificial Sequence
```

<220> FEATURE:
<223> OTHER INFORMATION: 2019-HR2P

<400> SEQUENCE: 1

```
Asp Ile Ser Gly Ile Asn Ala Ser Val Val Asn Ile Gln Lys Glu Ile
1               5                   10                  15

Asp Arg Leu Asn Glu Val Ala Lys Asn Leu Asn Glu Ser Leu Ile Asp
            20                  25                  30

Leu Gln Glu Leu
        35
```

<210> SEQ ID NO 2
<211> LENGTH: 36
<212> TYPE: PRT
<213> ORGANISM: Artificial Sequence
<220> FEATURE:
<223> OTHER INFORMATION: EK1

<400> SEQUENCE: 2

```
Ser Leu Asp Gln Ile Asn Val Thr Phe Leu Asp Leu Glu Tyr Glu Met
1               5                   10                  15

Lys Lys Leu Glu Glu Ala Ile Lys Lys Leu Glu Glu Ser Tyr Ile Asp
            20                  25                  30

Leu Lys Glu Leu
        35
```

<210> SEQ ID NO 3
<211> LENGTH: 42
<212> TYPE: PRT
<213> ORGANISM: Artificial Sequence
<220> FEATURE:
<223> OTHER INFORMATION: 2019-HR1P

<400> SEQUENCE: 3

```
Ala Asn Gln Phe Asn Ser Ala Ile Gly Lys Ile Gln Asp Ser Leu Ser
1               5                   10                  15

Ser Thr Ala Ser Ala Leu Gly Lys Leu Gln Asp Val Val Asn Gln Asn
            20                  25                  30

Ala Gln Ala Leu Asn Thr Leu Val Lys Gln
        35                  40
```

<210> SEQ ID NO 4
<211> LENGTH: 1295
<212> TYPE: PRT
<213> ORGANISM: Coronavirus

<400> SEQUENCE: 4

```
Met Pro Met Gly Ser Leu Gln Pro Leu Ala Thr Leu Tyr Leu Leu Gly
1               5                   10                  15

Met Leu Val Ala Ser Val Leu Ala Gln Cys Val Asn Leu Thr Thr Arg
            20                  25                  30

Thr Gln Leu Pro Pro Ala Tyr Thr Asn Ser Phe Thr Arg Gly Val Tyr
        35                  40                  45

Tyr Pro Asp Lys Val Phe Arg Ser Ser Val Leu His Ser Thr Gln Asp
    50                  55                  60

Leu Phe Leu Pro Phe Phe Ser Asn Val Thr Trp Phe His Ala Ile His
65                  70                  75                  80

Val Ser Gly Thr Asn Gly Thr Lys Arg Phe Asp Asn Pro Val Leu Pro
                85                  90                  95

Phe Asn Asp Gly Val Tyr Phe Ala Ser Thr Glu Lys Ser Asn Ile Ile
```

-continued

```
            100                 105                 110

Arg Gly Trp Ile Phe Gly Thr Thr Leu Asp Ser Lys Thr Gln Ser Leu
        115                 120                 125

Leu Ile Val Asn Asn Ala Thr Asn Val Val Ile Lys Val Cys Glu Phe
    130                 135                 140

Gln Phe Cys Asn Asp Pro Phe Leu Gly Val Tyr Tyr His Lys Asn Asn
145                 150                 155                 160

Lys Ser Trp Met Glu Ser Glu Phe Arg Val Tyr Ser Ser Ala Asn Asn
                165                 170                 175

Cys Thr Phe Glu Tyr Val Ser Gln Pro Phe Leu Met Asp Leu Glu Gly
            180                 185                 190

Lys Gln Gly Asn Phe Lys Asn Leu Arg Glu Phe Val Phe Lys Asn Ile
        195                 200                 205

Asp Gly Tyr Phe Lys Ile Tyr Ser Lys His Thr Pro Ile Asn Leu Val
    210                 215                 220

Arg Asp Leu Pro Gln Gly Phe Ser Ala Leu Glu Pro Leu Val Asp Leu
225                 230                 235                 240

Pro Ile Gly Ile Asn Ile Thr Arg Phe Gln Thr Leu Leu Ala Leu His
                245                 250                 255

Arg Ser Tyr Leu Thr Pro Gly Asp Ser Ser Ser Gly Trp Thr Ala Gly
            260                 265                 270

Ala Ala Ala Tyr Tyr Val Gly Tyr Leu Gln Pro Arg Thr Phe Leu Leu
        275                 280                 285

Lys Tyr Asn Glu Asn Gly Thr Ile Thr Asp Ala Val Asp Cys Ala Leu
    290                 295                 300

Asp Pro Leu Ser Glu Thr Lys Cys Thr Leu Lys Ser Phe Thr Val Glu
305                 310                 315                 320

Lys Gly Ile Tyr Gln Thr Ser Asn Phe Arg Val Gln Pro Thr Glu Ser
                325                 330                 335

Ile Val Arg Phe Pro Asn Ile Thr Asn Leu Cys Pro Phe Gly Glu Val
            340                 345                 350

Phe Asn Ala Thr Arg Phe Ala Ser Val Tyr Ala Trp Asn Arg Lys Arg
        355                 360                 365

Ile Ser Asn Cys Val Ala Asp Tyr Ser Val Leu Tyr Asn Ser Ala Ser
    370                 375                 380

Phe Ser Thr Phe Lys Cys Tyr Gly Val Ser Pro Thr Lys Leu Asn Asp
385                 390                 395                 400

Leu Cys Phe Thr Asn Val Tyr Ala Asp Ser Phe Val Ile Arg Gly Asp
                405                 410                 415

Glu Val Arg Gln Ile Ala Pro Gly Gln Thr Gly Lys Ile Ala Asp Tyr
            420                 425                 430

Asn Tyr Lys Leu Pro Asp Asp Phe Thr Gly Cys Val Ile Ala Trp Asn
        435                 440                 445

Ser Asn Asn Leu Asp Ser Lys Val Gly Gly Asn Tyr Asn Tyr Leu Tyr
    450                 455                 460

Arg Leu Phe Arg Lys Ser Asn Leu Lys Pro Phe Glu Arg Asp Ile Ser
465                 470                 475                 480

Thr Glu Ile Tyr Gln Ala Gly Ser Thr Pro Cys Asn Gly Val Glu Gly
                485                 490                 495

Phe Asn Cys Tyr Phe Pro Leu Gln Ser Tyr Gly Phe Gln Pro Thr Asn
            500                 505                 510

Gly Val Gly Tyr Gln Pro Tyr Arg Val Val Val Leu Ser Phe Glu Leu
        515                 520                 525
```

-continued

```
Leu His Ala Pro Ala Thr Val Cys Gly Pro Lys Lys Ser Thr Asn Leu
    530                 535                 540

Val Lys Asn Lys Cys Val Asn Phe Asn Phe Asn Gly Leu Thr Gly Thr
545                 550                 555                 560

Gly Val Leu Thr Glu Ser Asn Lys Lys Phe Leu Pro Phe Gln Gln Phe
                565                 570                 575

Gly Arg Asp Ile Ala Asp Thr Thr Asp Ala Val Arg Asp Pro Gln Thr
            580                 585                 590

Leu Glu Ile Leu Asp Ile Thr Pro Cys Ser Phe Gly Gly Val Ser Val
        595                 600                 605

Ile Thr Pro Gly Thr Asn Thr Ser Asn Gln Val Ala Val Leu Tyr Gln
    610                 615                 620

Asp Val Asn Cys Thr Glu Val Pro Val Ala Ile His Ala Asp Gln Leu
625                 630                 635                 640

Thr Pro Thr Trp Arg Val Tyr Ser Thr Gly Ser Asn Val Phe Gln Thr
                645                 650                 655

Arg Ala Gly Cys Leu Ile Gly Ala Glu His Val Asn Asn Ser Tyr Glu
            660                 665                 670

Cys Asp Ile Pro Ile Gly Ala Gly Ile Cys Ala Ser Tyr Gln Thr Gln
        675                 680                 685

Thr Asn Ser Pro Arg Arg Ala Arg Ser Val Ala Ser Gln Ser Ile Ile
    690                 695                 700

Ala Tyr Thr Met Ser Leu Gly Ala Glu Asn Ser Val Ala Tyr Ser Asn
705                 710                 715                 720

Asn Ser Ile Ala Ile Pro Thr Asn Phe Thr Ile Ser Val Thr Thr Glu
                725                 730                 735

Ile Leu Pro Val Ser Met Thr Lys Thr Ser Val Asp Cys Thr Met Tyr
            740                 745                 750

Ile Cys Gly Asp Ser Thr Glu Cys Ser Asn Leu Leu Leu Gln Tyr Gly
        755                 760                 765

Ser Phe Cys Thr Gln Leu Asn Arg Ala Leu Thr Gly Ile Ala Val Glu
    770                 775                 780

Gln Asp Lys Asn Thr Gln Glu Val Phe Ala Gln Val Lys Gln Ile Tyr
785                 790                 795                 800

Lys Thr Pro Pro Ile Lys Asp Phe Gly Gly Phe Asn Phe Ser Gln Ile
                805                 810                 815

Leu Pro Asp Pro Ser Lys Pro Ser Lys Arg Ser Phe Ile Glu Asp Leu
            820                 825                 830

Leu Phe Asn Lys Val Thr Leu Ala Asp Ala Gly Phe Ile Lys Gln Tyr
        835                 840                 845

Gly Asp Cys Leu Gly Asp Ile Ala Ala Arg Asp Leu Ile Cys Ala Gln
    850                 855                 860

Lys Phe Asn Gly Leu Thr Val Leu Pro Pro Leu Leu Thr Asp Glu Met
865                 870                 875                 880

Ile Ala Gln Tyr Thr Ser Ala Leu Leu Ala Gly Thr Ile Thr Ser Gly
                885                 890                 895

Trp Thr Phe Gly Ala Gly Ala Ala Leu Gln Ile Pro Phe Ala Met Gln
            900                 905                 910

Met Ala Tyr Arg Phe Asn Gly Ile Gly Val Thr Gln Asn Val Leu Tyr
        915                 920                 925

Glu Asn Gln Lys Leu Ile Ala Asn Gln Phe Asn Ser Ala Ile Gly Lys
    930                 935                 940
```

-continued

```
Ile Gln Asp Ser Leu Ser Ser Thr Ala Ser Ala Leu Gly Lys Leu Gln
945                 950                 955                 960

Asp Val Val Asn Gln Asn Ala Gln Ala Leu Asn Thr Leu Val Lys Gln
                965                 970                 975

Leu Ser Ser Asn Phe Gly Ala Ile Ser Ser Val Leu Asn Asp Ile Leu
            980                 985                 990

Ser Arg Leu Asp Lys Val Glu Ala  Glu Val Gln Ile Asp  Arg Leu Ile
        995                 1000                1005

Thr Gly  Arg Leu Gln Ser Leu  Gln Thr Tyr Val Thr  Gln Gln Leu
    1010                1015                1020

Ile Arg  Ala Ala Glu Ile Arg  Ala Ser Ala Asn Leu  Ala Ala Thr
    1025                1030                1035

Lys Met  Ser Glu Cys Val Leu  Gly Gln Ser Lys Arg  Val Asp Phe
    1040                1045                1050

Cys Gly  Lys Gly Tyr His Leu  Met Ser Phe Pro Gln  Ser Ala Pro
    1055                1060                1065

His Gly  Val Val Phe Leu His  Val Thr Tyr Val Pro  Ala Gln Glu
    1070                1075                1080

Lys Asn  Phe Thr Thr Ala Pro  Ala Ile Cys His Asp  Gly Lys Ala
    1085                1090                1095

His Phe  Pro Arg Glu Gly Val  Phe Val Ser Asn Gly  Thr His Trp
    1100                1105                1110

Phe Val  Thr Gln Arg Asn Phe  Tyr Glu Pro Gln Ile  Ile Thr Thr
    1115                1120                1125

Asp Asn  Thr Phe Val Ser Gly  Asn Cys Asp Val Val  Ile Gly Ile
    1130                1135                1140

Val Asn  Asn Thr Val Tyr Asp  Pro Leu Gln Pro Glu  Leu Asp Ser
    1145                1150                1155

Phe Lys  Glu Glu Leu Asp Lys  Tyr Phe Lys Asn His  Thr Ser Pro
    1160                1165                1170

Asp Val  Asp Leu Gly Asp Ile  Ser Gly Ile Asn Ala  Ser Val Val
    1175                1180                1185

Asn Ile  Gln Lys Glu Ile Asp  Arg Leu Asn Glu Val  Ala Lys Asn
    1190                1195                1200

Leu Asn  Glu Ser Leu Ile Asp  Leu Gln Glu Leu Gly  Lys Tyr Glu
    1205                1210                1215

Gln Tyr  Ile Lys Trp Pro Trp  Tyr Ile Trp Leu Gly  Phe Ile Ala
    1220                1225                1230

Gly Leu  Ile Ala Ile Val Met  Val Thr Ile Met Leu  Cys Cys Met
    1235                1240                1245

Thr Ser  Cys Cys Ser Cys Leu  Lys Gly Cys Cys Ser  Cys Gly Ser
    1250                1255                1260

Cys Cys  Lys Phe Asp Glu Asp  Asp Ser Glu Pro Val  Leu Lys Gly
    1265                1270                1275

Val Lys  Leu His Tyr Thr Gly  Gly Thr Glu Thr Ser  Gln Val Ala
    1280                1285                1290

Pro Ala
    1295


<210> SEQ ID NO 5
<211> LENGTH: 3906
<212> TYPE: DNA
<213> ORGANISM: Coronavirus

<400> SEQUENCE: 5
```

```
ggatccgcca ccatgcccat ggggtctctg caaccgctgg ccaccttgta cctgctgggg     60
atgctggtcg cttccgtgct agcccagtgc gtgaacctga ccacaaggac ccagctgccc    120
cctgcctata ccaattcctt cacacggggc gtgtactatc ccgacaaggt gtttagaagc    180
tccgtgctgc actctacaca ggatctgttt ctgcctttct ttagcaacgt gacctggttc    240
cacgccatcc acgtgagcgg caccaatggc acaaagcggt tcgacaatcc agtgctgccc    300
tttaacgatg gcgtgtactt cgcctctacc gagaagagca acatcatcag aggctggatc    360
tttggcacca cactggactc caagacacag tctctgctga tcgtgaacaa tgccaccaac    420
gtcgtgatca aggtgtgcga gttccagttt tgtaatgatc ctttcctggg cgtgtactat    480
cacaagaaca ataagagctg gatggagtcc gagtttcgcg tgtattctag cgccaacaat    540
tgcacatttg agtacgtgtc ccagccattc ctgatggacc tggagggcaa gcagggcaat    600
ttcaagaacc tgagggagtt cgtgtttaag aatatcgatg gctacttcaa gatctactct    660
aagcacaccc caatcaacct ggtgcgcgac ctgccacagg gcttcagcgc cctggagcca    720
ctggtggatc tgcccatcgg catcaacatc acccggtttc agacactgct ggccctgcac    780
agaagctacc tgacacctgg cgactcctct agcggatgga ccgcaggagc tgccgcctac    840
tatgtgggct atctgcagcc aaggaccttc ctgctgaagt acaacgagaa tggcaccatc    900
acagacgcag tggattgcgc actggacccc ctgagcgaga ccaagtgtac actgaagtcc    960
tttaccgtgg agaagggcat ctatcagaca tccaatttca gggtgcagcc caccgagtct   1020
atcgtgcgct ttcccaatat cacaaacctg tgcccttttg gcgaggtgtt caacgcaacc   1080
aggttcgcaa gcgtgtacgc atggaatagg aagcggatca gcaactgcgt ggccgactat   1140
agcgtgctgt acaactccgc ctctttcagc acctttaagt gctatggcgt gtcccccaca   1200
aagctgaatg acctgtgctt taccaacgtg tacgccgatt ctttcgtgat caggggcgac   1260
gaggtgcgcc agatcgcacc aggacagaca ggcaagatcg cagactacaa ttataagctg   1320
cctgacgatt tcaccggctg cgtgatcgcc tggaacagca acaatctgga ttccaaagtg   1380
ggcggcaact acaattatct gtaccggctg tttagaaagt ctaatctgaa gccattcgag   1440
agggacatct ctacagagat ctaccaggca ggcagcaccc catgcaatgg agtggagggc   1500
tttaactgtt atttccctct gcagagctac ggcttccagc caacaaacgg cgtgggctat   1560
cagccctacc gcgtggtggt gctgagcttt gagctgctgc acgcacctgc aacagtgtgc   1620
ggaccaaaga agtccaccaa tctggtgaag aacaagtgcg tgaacttcaa cttcaacgga   1680
ctgaccggca caggcgtgct gaccgagtcc aacaagaagt tcctgccctt tcagcagttc   1740
ggcagggaca tcgcagatac cacagacgcc gtgcgcgacc ctcagaccct ggagatcctg   1800
gacatcacac catgctcttt cggcggcgtg agcgtgatca cacctggcac caatacaagc   1860
aaccaggtgg ccgtgctgta tcaggacgtg aattgtaccg aggtgcccgt ggcaatccac   1920
gcagatcagc tgacccctac atggcgggtg tacagcaccg gctccaacgt gttccagaca   1980
agagccggat gcctgatcgg agcagagcac gtgaacaatt cctatgagtg cgacatccct   2040
atcggcgccg gcatctgtgc ctcttaccag acccagacaa actctccaag gagagcccgg   2100
agcgtggcat cccagtctat catcgcctat acaatgagcc tgggcgccga gaacagcgtg   2160
gcctactcta acaatagcat cgccatccct accaacttca caatctccgt gaccacagag   2220
atcctgccag tgtccatgac caagacatct gtggactgca caatgtatat ctgtggcgat   2280
tctaccgagt gcagcaacct gctgctgcag tacggcagct tttgtaccca gctgaataga   2340
```

```
gccctgacag gcatcgccgt ggagcaggac aagaacacac aggaggtgtt cgcccaggtg   2400

aagcagatct acaagacccc acccatcaag gactttggcg gcttcaattt ttcccagatc   2460

ctgcccgatc cttccaagcc ttctaagcgg agctttatcg aggacctgct gttcaacaag   2520

gtgaccctgg ccgatgccgg cttcatcaag cagtatggcg attgcctggg cgacatcgcc   2580

gccagagacc tgatctgtgc ccagaagttt aatggcctga ccgtgctgcc tccactgctg   2640

acagatgaga tgatcgcaca gtacacaagc gccctgctgg caggcaccat cacatccgga   2700

tggaccttcg gcgcaggagc cgccctgcag atccccttcg ctatgcagat ggcctatcgg   2760

ttcaacggca tcggcgtgac ccagaatgtg ctgtacgaga accagaagct gatcgccaat   2820

cagtttaact ccgccatcgg caagatccag gacagcctgt cctctacagc ctccgccctg   2880

ggcaagctgc aggatgtggt gaatcagaac gcccaggccc tgaataccct ggtgaagcag   2940

ctgagctcca acttcggcgc catctctagc gtgctgaatg acatcctgag ccggctggac   3000

aaggtggagg cagaggtgca gatcgaccgg ctgatcacag gcagactgca gtctctgcag   3060

acctacgtga cacagcagct gatcagggca gcagagatca gggcaagcgc caatctggca   3120

gcaaccaaga tgtccgagtg cgtgctgggc cagtctaaga gagtggactt ttgtggcaag   3180

ggctatcacc tgatgtcctt cccacagtct gcccctcacg gagtggtgtt tctgcacgtg   3240

acctacgtgc cagcccagga gaagaacttc accacagcac cagcaatctg ccacgatggc   3300

aaggcacact ttcccaggga gggcgtgttc gtgagcaacg gcacccactg gtttgtgaca   3360

cagcgcaatt tctacgagcc tcagatcatc accacagaca atacattcgt gtccggcaac   3420

tgtgacgtgg tcatcggcat cgtgaacaat accgtgtatg atcctctgca gccagagctg   3480

gacagcttta aggaggagct ggataagtac ttcaagaatc acacctcccc agacgtggat   3540

ctgggcgaca tcagcggcat caatgcctcc gtggtgaaca tccagaagga gatcgacagg   3600

ctgaacgagg tggccaagaa tctgaacgag agcctgatcg atctgcagga gctgggcaag   3660

tatgagcagt acatcaagtg gccctggtat atctggctgg gcttcatcgc cggcctgatc   3720

gctatcgtga tggtgaccat catgctgtgc tgtatgacat cctgctgttc ttgcctgaag   3780

ggctgctgta gctgtggctc ctgctgtaag tttgatgagg acgattccga gccagtgctg   3840

aagggcgtga agctgcacta caccggcggc accgagacat ctcaggtggc cccgcctaa    3900

ctcgag                                                              3906


<210> SEQ ID NO 6
<211> LENGTH: 5
<212> TYPE: PRT
<213> ORGANISM: Artificial Sequence
<220> FEATURE:
<223> OTHER INFORMATION: linker
<220> FEATURE:
<221> NAME/KEY: REPEAT
<222> LOCATION: (1)..(5)
<223> OTHER INFORMATION: repeat number is any integer

<400> SEQUENCE: 6

Gly Ser Gly Ser Gly
1               5


<210> SEQ ID NO 7
<211> LENGTH: 40
<212> TYPE: PRT
<213> ORGANISM: Artificial Sequence
<220> FEATURE:
<223> OTHER INFORMATION: Palmitic acid modified polypeptide
<220> FEATURE:
```

<221> NAME/KEY: REPEAT
<222> LOCATION: (37)..(39)
<223> OTHER INFORMATION: repeat number is any interger
<220> FEATURE:
<221> NAME/KEY: MOD_RES
<222> LOCATION: (39)..(39)
<223> OTHER INFORMATION: PEG4 modified
<220> FEATURE:
<221> NAME/KEY: MOD_RES
<222> LOCATION: (40)..(40)
<223> OTHER INFORMATION: palmitic acid modification

<400> SEQUENCE: 7

Ser Leu Asp Gln Ile Asn Val Thr Phe Leu Asp Leu Glu Tyr Glu Met
1               5                   10                  15

Lys Lys Leu Glu Glu Ala Ile Lys Lys Leu Glu Glu Ser Tyr Ile Asp
            20                  25                  30

Leu Lys Glu Leu Gly Ser Gly Lys
        35                  40

<210> SEQ ID NO 8
<211> LENGTH: 42
<212> TYPE: PRT
<213> ORGANISM: Artificial Sequence
<220> FEATURE:
<223> OTHER INFORMATION: cholesterol modified polypeptide
<220> FEATURE:
<221> NAME/KEY: REPEAT
<222> LOCATION: (37)..(41)
<223> OTHER INFORMATION: n is any integer.
<220> FEATURE:
<221> NAME/KEY: MOD_RES
<222> LOCATION: (41)..(41)
<223> OTHER INFORMATION: PEG4 modified
<220> FEATURE:
<221> NAME/KEY: MOD_RES
<222> LOCATION: (42)..(42)
<223> OTHER INFORMATION: cholesterol modified

<400> SEQUENCE: 8

Ser Leu Asp Gln Ile Asn Val Thr Phe Leu Asp Leu Glu Tyr Glu Met
1               5                   10                  15

Lys Lys Leu Glu Glu Ala Ile Lys Lys Leu Glu Glu Ser Tyr Ile Asp
            20                  25                  30

Leu Lys Glu Leu Gly Ser Gly Ser Gly Cys
        35                  40

<210> SEQ ID NO 9
<211> LENGTH: 40
<212> TYPE: PRT
<213> ORGANISM: Artificial Sequence
<220> FEATURE:
<223> OTHER INFORMATION: palmitic acid modified polypeptide
<220> FEATURE:
<221> NAME/KEY: MOD_RES
<222> LOCATION: (39)..(39)
<223> OTHER INFORMATION: PEG4 modified
<220> FEATURE:
<221> NAME/KEY: MOD_RES
<222> LOCATION: (40)..(40)
<223> OTHER INFORMATION: palmitic acid modified

<400> SEQUENCE: 9

Ser Leu Asp Gln Ile Asn Val Thr Phe Leu Asp Leu Glu Tyr Glu Met
1               5                   10                  15

Lys Lys Leu Glu Glu Ala Ile Lys Lys Leu Glu Glu Ser Tyr Ile Asp
            20                  25                  30

Leu Lys Glu Leu Gly Ser Gly Lys 35 40

<210> SEQ ID NO 10
<211> LENGTH: 42
<212> TYPE: PRT
<213> ORGANISM: Artificial Sequence
<220> FEATURE:
<223> OTHER INFORMATION: cholesterol modified polypeptide
<220> FEATURE:
<221> NAME/KEY: MOD_RES
<222> LOCATION: (41)..(41)
<223> OTHER INFORMATION: PEG4 modified
<220> FEATURE:
<221> NAME/KEY: MOD_RES
<222> LOCATION: (42)..(42)
<223> OTHER INFORMATION: cholesterol modified

<400> SEQUENCE: 10

Ser Leu Asp Gln Ile Asn Val Thr Phe Leu Asp Leu Glu Tyr Glu Met
1 5 10 15

Lys Lys Leu Glu Glu Ala Ile Lys Lys Leu Glu Glu Ser Tyr Ile Asp
20 25 30

Leu Lys Glu Leu Gly Ser Gly Ser Gly Cys
35 40

<210> SEQ ID NO 11
<211> LENGTH: 5
<212> TYPE: PRT
<213> ORGANISM: Artificial Sequence
<220> FEATURE:
<223> OTHER INFORMATION: PEGylated linker
<220> FEATURE:
<221> NAME/KEY: REPEAT
<222> LOCATION: (1)..(5)
<223> OTHER INFORMATION: repeat number is any interger
<220> FEATURE:
<221> NAME/KEY: MOD_RES
<222> LOCATION: (5)..(5)
<223> OTHER INFORMATION: PEG modified

<400> SEQUENCE: 11

Gly Ser Gly Ser Gly
1 5

<210> SEQ ID NO 12
<211> LENGTH: 5
<212> TYPE: PRT
<213> ORGANISM: Artificial Sequence
<220> FEATURE:
<223> OTHER INFORMATION: linker
<220> FEATURE:
<221> NAME/KEY: REPEAT
<222> LOCATION: (1)..(5)
<223> OTHER INFORMATION: repeat number is 1 or 2

<400> SEQUENCE: 12

Gly Ser Gly Ser Gly
1 5

<210> SEQ ID NO 13
<211> LENGTH: 40
<212> TYPE: PRT
<213> ORGANISM: Artificial Sequence
<220> FEATURE:
<223> OTHER INFORMATION: PEGylated linker
<220> FEATURE:
<221> NAME/KEY: REPEAT
<222> LOCATION: (37)..(39)
<223> OTHER INFORMATION: repeat number is 1 or 2
<220> FEATURE:

-continued

```
<221> NAME/KEY: MOD_RES
<222> LOCATION: (39)..(39)
<223> OTHER INFORMATION: PEG4 modified
<220> FEATURE:
<221> NAME/KEY: MOD_RES
<222> LOCATION: (40)..(40)
<223> OTHER INFORMATION: palmitic acid modified

<400> SEQUENCE: 13

Ser Leu Asp Gln Ile Asn Val Thr Phe Leu Asp Leu Glu Tyr Glu Met
1               5                   10                  15

Lys Lys Leu Glu Glu Ala Ile Lys Lys Leu Glu Glu Ser Tyr Ile Asp
            20                  25                  30

Leu Lys Glu Leu Gly Ser Gly Lys
        35                  40


<210> SEQ ID NO 14
<211> LENGTH: 42
<212> TYPE: PRT
<213> ORGANISM: Artificial Sequence
<220> FEATURE:
<223> OTHER INFORMATION: cholesterol modified polypeptide
<220> FEATURE:
<221> NAME/KEY: REPEAT
<222> LOCATION: (37)..(41)
<223> OTHER INFORMATION: n is 1 or 2
<220> FEATURE:
<221> NAME/KEY: MOD_RES
<222> LOCATION: (41)..(41)
<223> OTHER INFORMATION: PEG4 modified
<220> FEATURE:
<221> NAME/KEY: MOD_RES
<222> LOCATION: (42)..(42)
<223> OTHER INFORMATION: cholesterol modified

<400> SEQUENCE: 14

Ser Leu Asp Gln Ile Asn Val Thr Phe Leu Asp Leu Glu Tyr Glu Met
1               5                   10                  15

Lys Lys Leu Glu Glu Ala Ile Lys Lys Leu Glu Glu Ser Tyr Ile Asp
            20                  25                  30

Leu Lys Glu Leu Gly Ser Gly Ser Gly Cys
        35                  40
```

POLYPEPTIDE, AND PREPARATION METHOD THEREFOR AND USE THEREOF

This application claims priority of Chinese patent application filed on Feb. 5, 2020, titled "Polypeptide, preparation method and use thereof" with the application number of 202010080751.4, which is incorporated herein by reference.

FIELD OF THE INVENTION

The present invention relates to the field of polypeptide therapeutics, and more specifically relates to polypeptides that inhibit coronaviruses.

BACKGROUND OF THE INVENTION

The novel coronavirus may be transmitted to humans by certain animals. The pathogen was quickly identified as a new type of coronavirus, and the World Health Organization named it as 2019-nCoV [*J. Med. Virol.* 2020. 92, doi: 10.1002/jmv.25678]. Subsequently, the International Committee on Taxonomy of Viruses named the novel coronavirus as SARS-CoV-2.

Therefore, methods and specific drugs to effectively prevent and control the spread of the coronaviruses have become important tasks that need to be solved urgently.

SUMMARY OF THE INVENTION

The present invention discloses a polypeptide that can inhibit the infection of a novel coronavirus (2019-nCoV). The inventors discovered a polypeptide or polypeptide derivative that can inhibit 2019-nCoV infection alone based on the HR1 target in the S2 region of the S protein on 2019-nCoV. They can also have a good inhibitory effect on other coronaviruses that may infect humans, such as SARS-like viruses (Rs3367-CoV or WIV1-CoV). The present invention provides a good preventive and therapeutic candidate drug for 2019-nCoV that is still circulating at present and SARS-like viruses that may break out in the future.

In one aspect, the present invention provides a polypeptide, which is:

(1) a polypeptide comprising the amino acid sequence shown in SEQ ID NO. 1;

(2) a polypeptide comprising an amino acid sequence in which one or more amino acid residues are substituted, deleted, added or inserted in the amino acid sequence shown in SEQ ID NO. 1, wherein the polypeptide has an inhibitory activity against coronavirus; or (3) a polypeptide comprising an amino acid sequence having at least 60%, 65%, 70%, 75%, 80%, 85%, 90%, 93%, 94% or 95% identity with the amino acid sequence shown in SEQ ID NO. 1, wherein the polypeptide has an inhibitory activity against coronavirus.

In one aspect, the present invention further provides a fusion protein or conjugate comprising the polypeptide of the present invention.

In one aspect, the present invention further provides a nucleic acid encoding the polypeptide of the present invention or the fusion protein of the present invention.

In one aspect, the present invention further provides a vector comprising the nucleic acid of the present invention.

In one aspect, the present invention further provides a host cell comprising the vector of the present invention.

In one aspect, the present invention further provides a method for preparing the polypeptide or the fusion protein of the present invention, which comprises the following steps:

(1) introducing the vector according to the present invention into a host cell;

(2) culturing the host cell in a suitable medium; and (3) harvesting and isolating the polypeptide or the fusion protein.

In one aspect, the present invention further provides a polypeptide derivative, which is a derivative obtained by palmitoylation modification or cholesterol modification of the polypeptide described in any one of (1) to (3) below:

(1) a polypeptide comprising the amino acid sequence shown in SEQ ID NO. 2;

(2) a polypeptide comprising an amino acid sequence in which one or more amino acid residues are substituted, deleted, added or inserted in the amino acid sequence shown in SEQ ID NO. 2, wherein the polypeptide has an inhibitory activity against coronavirus;

(3) a polypeptide comprising an amino acid sequence having at least 60%, 65%, 70%, 75%, 80%, 85%, 90%, 93%, 94% or 95% identity with the amino acid sequence shown in SEQ ID NO. 2, wherein the polypeptide has inhibitory activity against coronavirus.

In one embodiment, the palmitoylation modification or cholesterol modification is performed at the C-terminus of the polypeptide.

In one embodiment, the polypeptide is linked to the palmitic acid or cholesterol moiety via a linker at the C-terminus.

In one embodiment, the linker is PEGylated. For example, the linker can be PEGylated with dPEG.

In one embodiment, the polypeptide is linked to palmitoylation modified lysine or cholesterol modified cysteine via a linker at the C-terminus. In other words, the polypeptide is linked to palmitic acid or cholesterol moiety via a linker via lysine or cysteine.

In one embodiment, the linker comprises (GSG)n or (GSGSG)n, wherein n may be any integer. For example, n is 1, 2, 3, 4, or 5.

In one embodiment, the linker is -(GSG)n-DPEG4- or -(GSGSG)n-DPEG4-(SEQ ID NO: 11), wherein n may be any integer. For example, n is 1, 2, 3, 4, or 5.

In one embodiment, the polypeptide derivative is SLDQINVTFLDLEYEMKKLEEAIKKLEESYIDLKEL-(GSG)n-DPEG4-K-palmitic acid (SEQ ID NO: 7) or SLDQINVTFLDLEYEMKKLEEAIKKLEESYIDLKEL-(GSGSG)n-DPEG4-C-cholesterol (SEQ ID NO: 8). N may be any integer. For example, n is 1, 2, 3, 4, or 5.

In one embodiment, the polypeptide derivative is SLDQINVTFLDLEYEMKKLEEAIKKLEESYIDLKEL-GSG-DPEG4-K-palmitic acid (SEQ ID NO: 9) or SLDQINVTFLDLEYEMKKLEEAIKKLEESYIDLKEL-GSGSG-DPEG4-C-cholesterol (SEQ ID NO: 10).

In one aspect, the present invention further provides a composition comprising the polypeptide of the present invention and/or the polypeptide or derivative of the present invention.

In one embodiment, the composition is an external preparation. In one embodiment, the composition is an external liniment. In one embodiment, the composition is an external gel or external infiltration preparation.

In one embodiment, the composition further comprises an agent for inhibiting coronavirus or treating and/or preventing a disease caused by coronavirus. The agent can be selected from the group consisting of favipiravir, nelfinavir, arbidol, lopinavir, ritonavir, darunavir, chloroquine phosphate, or remdesivir. In one embodiment, the composition comprises a pharmaceutically acceptable carrier.

In one aspect, the present invention provides use of the polypeptide, the fusion protein or conjugate, the nucleic acid, the vector, the host cell, the polypeptide or polypeptide derivative or the composition of the present invention in the manufacture of a medicament for inhibiting coronavirus or treating and/or preventing a disease caused by coronavirus.

In one embodiment, the coronavirus is 2019-nCoV, Rs3367-CoV and/or WIV1-CoV.

In one embodiment, the dosage form of the medicament is tablet, capsule, dripping pill, aerosol, pill, powder, solution, suspension, emulsion, granule, liposome, transdermal agent, suppository or lyophilized powder injection.

In one embodiment, the medicament is preferably administered by the followings: injection, including subcutaneous injection, intravenous injection, intramuscular injection and intraperitoneal injection, intracisternal injection or infusion, etc., cavity administration, such as rectal, vaginal and sublingual, respiratory administration, such as through the nasal cavity; mucosal administration, or topical administration.

In one aspect, the present invention provides a method for inhibiting coronavirus in vitro, comprising using the polypeptide, the fusion protein or conjugate, the nucleic acid, the vector, the host cell, the polypeptide derivative or the composition of the present invention.

In one embodiment, the coronavirus is 2019-nCoV, Rs3367-CoV or WIV1-CoV.

DETAILED DESCRIPTION OF THE INVENTION

Figure 1:
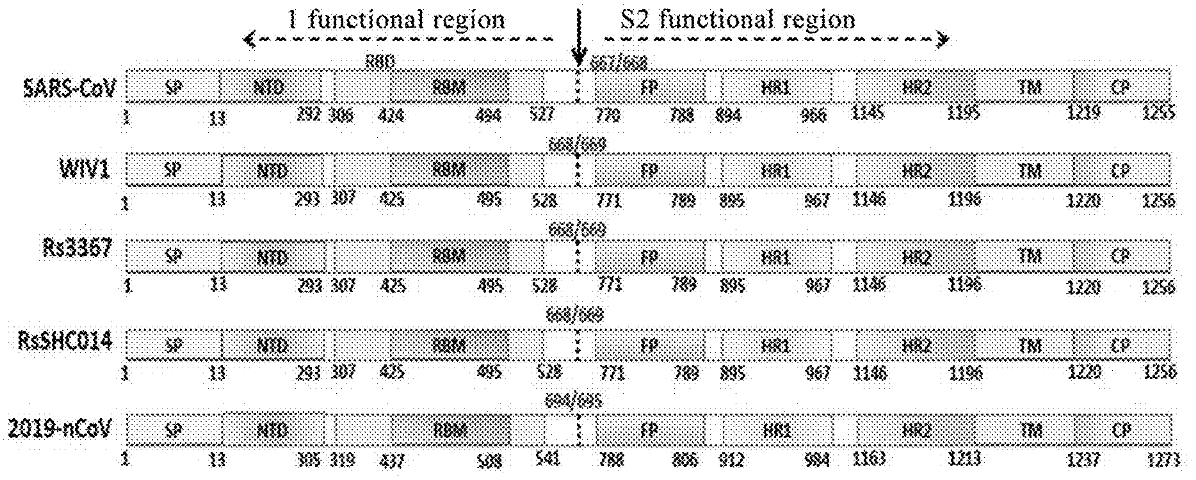
FIG. 1: A diagram of sequence analysis of 2019-nCoV and SARS-like virus S protein.

During the process of infecting target cells by human coronaviruses, its Spike glycoprotein (S protein) plays a critical role. S protein can be divided into S1 subunit and S2 subunit. The S1 subunit comprises two functional domains, an N-terminal domain (NTD) and a receptor binding domain (RBD), both of which are responsible for the binding of the virus to the host cell receptor. They also comprise several conformational neutralizing epitopes, which are targets for the development of neutralizing antibodies and vaccines. The S2 subunit comprises three functional domains, a fusion peptide (FP) and two heptad repeat regions (HR), HR1 and HR2. After the RBD in S1 binds to the receptor, the conformation of the S2 subunit is changed by inserting FP into the host cell membrane, and then the HR1 and HR2 regions form a six-helix bundle (6-HB), causing the viral membrane to fuse with the cell membrane, and the genetic material of the virus enters the target cell through the fusion pore to replicate to produce new virus particles. The S2 region of S protein is an important target for drug design. The polypeptide (SC-1) derived from the HR2 domain of the SARS-CoV S protein can interact with the HR1 region of the virus S protein to form a heterologous 6-HB, inhibiting the formation of the homologous 6-HB between the HR1 and HR2 domains, thereby blocking the fusion of the virus and the host cell. However, the activity of this polypeptide is very poor (IC50 of 20 μM), making it difficult to be further developed as a clinical drug. Polypeptides with the same mechanism of action have been approved for the treatment of HIV. For example, Enfuvirtide (Fuzeon, also known as T20), the first polypeptide HIV entry inhibitor in the world approved by the US FDA, is currently used in the clinical treatment of AIDS. Professor Jiang Shibo (one of the inventors of this patent) is the inventor of the Enfuvirtide prototype polypeptide (U.S. Pat. No. 5,444,044).

For the current outbreak of 2019-nCoV, there are currently no specific drugs targeting the virus, including polypeptide inhibitors for the S2 region. The present invention first designed a set of polypeptide inhibitors targeting this region based on the sequence characteristics of the HR1 target site on the S2 region of the virus and the feature that key amino acid sites are relatively conservative. The experimental results found that these polypeptides can effectively inhibit the virus membrane fusion and pseudovirus infection, and have the potential to be developed into highly effective anti-2019-nCoV specific drugs. At the same time, we also found that the designed polypeptide can also effectively inhibit a variety of SARS-like viruses from bats. Therefore, the present invention can provide a good preventive and therapeutic candidate drug for the 2019-nCoV that is still circulating and the SARS-like viruses that may break out in the future.

The purpose of the present invention is to provide a set of entry inhibitory polypeptides that can inhibit 2019-nCoV and SARS-like virus infections. The entry inhibitory polypeptides bind to the HR1 region in the S2 protein of 2019-nCoV and SARS-like viruses, and interferes with the 6HB formation process of the virus, thereby inhibiting the fusion and infection processes of the virus. The sequences of this set of polypeptides are shown in Table 4, or detailed in the polypeptide sequence listing. The important innovation point of this invention is that the polypeptides have inhibitory activity against newly outbroken 2019-nCoV, and the inhibitory activity of some polypeptides has reached an unexpectedly high level.

One of the objectives of the present invention is to provide a polypeptide or polypeptide derivative that inhibits coronavirus or has an inhibitory function on coronavirus infection. This is achieved by binding to the HR1 region in the S2 protein of the coronavirus. The coronavirus can be 2019-nCoV, SARS-like virus Rs3367-CoV or WIV1-CoV.

Herein, the polypeptide may be a polypeptide comprising SEQ ID NO: 1 or 2 or a variant thereof.

For example, the polypeptide may include an amino acid sequence in which one or more, preferably 2, 3, 4 or 5 amino acid residues are substituted, added, deleted or inserted in the amino acid sequence shown in SEQ ID NO: 1 or 2.

Amino acid addition refers to the addition of amino acids to the C-terminus or N-terminus of an amino acid sequence, such as SEQ ID NO: 1 or 2, as long as the polypeptide has inhibitory activity against coronavirus.

Amino acid substitution refers to the replacement of a certain amino acid residue at a certain position in the amino acid sequence, such as SEQ ID NO: 1 or 2, by another amino acid residue, as long as the polypeptide has inhibitory activity against coronavirus.

Amino acid insertion refers to the insertion of amino acid residues at appropriate positions in the amino acid sequence, such as the sequence of SEQ ID NO: 1 or 2. The inserted amino acid residues may be either adjacent to each other in whole or in part, or not adjacent to each other, as long as the polypeptide has inhibitory activity against the coronavirus.

Amino acid deletion refers to the deletion of 1, 2, 3 or more amino acids from the amino acid sequence, such as the sequence of SEQ ID NO: 1 or 2, as long as the polypeptide has inhibitory activity against the coronavirus.

In the present invention, the substitution may be a conservative amino acid substitution, which means that compared with the amino acid sequence of SEQ ID NO: 1 or 2, 3, preferably 2 amino acids or 1 amino acid are replaced by amino acids with similar properties to form peptides. These conservative variant peptides can be produced by amino acid substitutions according to Table 1.

In the context of the present invention, conservative substitutions can be defined in terms of substitutions within the amino acid classes reflected in one or more of the following three tables:

TABLE 1

| Amino acid residue classes for conservative substitutions | |
|---|---|
| Acidic Residues | Asp (D) and Glu (E) |
| Basic Residues | Lys (K), Arg (R), and His (H) |
| Hydrophilic Uncharged Residues | Ser (S), Thr (T), Asn (N), and Gln (Q) |
| Aliphatic Uncharged Residues | Gly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

TABLE 2

| Alternative conservative amino acid residue substitution classes | | | |
|---|---|---|---|
| 1 | A | S | T |
| 2 | D | E | |
| 3 | N | Q | |
| 4 | R | K | |
| 5 | I | L | M |
| 6 | F | Y | W |

TABLE 3

| Alternative physical and functional classifications of amino acid residues | |
|---|---|
| Alcohol group-containing residues | S and T |
| Aliphatic residues | I, L, V, and M |
| Cycloalkenyl-associated residues | F, H, W, and Y |
| Hydrophobic residues | A, C, F, G, H, I, L, M, R, T, V, W, and Y |
| Negatively charged residues | D and E |
| Polar residues | C, D, E, H, K, N, Q, R, S, and T |
| Positively charged residues | H, K, and R |
| Small residues | A, C, D, G, N, P, S, T, and V |
| Very small residues | A, G, and S |

TABLE 3-continued

| Alternative physical and functional classifications of amino acid residues | |
|---|---|
| Residues involved in turn formation | A, C, D, E, G, H, K, N, Q, R, S, P, and T |
| Flexible residues | Q, T, K, S, G, N, D, E, and R |

For purposes of the present invention, the sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment).

The present invention also provides a fusion protein or conjugate comprising the polypeptide of the present invention, such as SEQ ID NO. 1 or 2, as long as the fusion protein or conjugate has the coronavirus inhibitory activity of the polypeptide of the present invention. Those skilled in the art are fully aware of the preparation methods of fusion proteins or conjugates. For example, the polypeptide of the present invention can be fused or conjugated to another functional moiety directly or indirectly through a linker. Another functional moiety can be a cholesterol moiety, palmitic acid moiety, carrier protein, active protein, marker protein and the like. The polypeptide can be modified by myristoylation, or stearic acid, or palmitic acid, or cholesterol, amidation, or isoprenylation.

The polypeptide of the present invention may be produced synthetically or the polypeptide of the present invention may be expressed by cells. For example, the polypeptide of the present invention can be synthesized by chemical means. Alternatively, the polypeptide of the invention can be expressed in recombinant cells. The type of cell is not limited, for example, the cell may be a eukaryotic cell or a prokaryotic cell. Eukaryotic cells may be fungal cells, such as yeast cells, or insect cells or mammalian cells, such as mouse cells. The prokaryotic cell may be a bacterial cell, such as an *E. coli* cell.

The nucleic acid encoding the polypeptide of the present invention can be codon optimized according to the host cell used. The nucleic acid can be cloned into a suitable expression vector, which can be then introduced into a host cell for expression. The type of expression vector is not limited and is well known to those skilled in the art.

The invention also provides a method for preparing the polypeptide or fusion protein. The method comprises introducing the expression vector into the host cells, which are then cultured in a suitable medium, and then harvesting or isolating the polypeptides or fusion proteins in the supernatant, or in the context of intracellular expression, the host cells can be collected, and then the cells can be lysed to collect these polypeptides or fusion proteins. In the context of a polypeptide or fusion protein, the polypeptide or fusion protein can be linked to a suitable signal peptide. The signal peptide is cleaved or not after harvest. These techniques are well known to those skilled in the art.

The polypeptides of the present invention can be prepared in the form of derivatives. For example, the polypeptide can be modified by palmitoylation or cholesterol modification. The method of palmitoylation modification or cholesterol modification is well known. In one embodiment, palmitoylation or cholesterol modification can be performed at the C-terminus of the polypeptide, so that the polypeptide is linked to palmitic acid or cholesterol moiety at the C-terminus. The linkage can be a direct connection or can be connected through a linker.

The type and length of the linker can vary. For example, the linker can be (GSG)n or (GSGSG)n (SEQ ID NO: 6), wherein n can be any integer, such as 1, 2, 3, 4, 5, 6, and so on.

The linker can be PEGylated. The means of PEGylation modification are known to those skilled in the art. As used herein, the term PEGylated linker refers to the linker with one or more PEG attached. Here, the PEGylated linker can be PEGylated (GSG)n or (GSGSG)n (SEQ ID NO: 11). n can be any integer, such as 1, 2, 3, 4, 5, 6, and so on.

As used herein, "DPEG" refers to discrete polyethylene glycol. DPEG4 indicates that the number of repeated ethylene glycol residues is 4.

As used herein, the coronavirus can be any kind of coronavirus. Preferably, the coronavirus is 2019-nCoV, Rs3367-CoV or WIV1-CoV.

The polypeptides or polypeptide derivatives of the present invention can be used alone or in combination, or in combination with other agents having anti-coronavirus activity or coronavirus inhibitory activity. For example, these agents may be agents that have been reported to have inhibitory activity against coronaviruses or have therapeutic effects against coronavirus diseases, such as coronavirus pneumonia, such as favipiravir, nelfinavir, arbidol, lopinavir, ritonavir, chloroquine phosphate, darunavir or remdesivir, and so on.

Herein, the polypeptide or polypeptide derivative of the present invention may include 2019-HR2P, EK1, EK1-plam, and EK1-chol. They can be prepared in the form of a composition for application. The composition may comprise a suitable carrier, such as a pharmaceutically acceptable carrier. Such a composition can be used for external use, for example, as an external preparation, an external liniment, such as an external gel or external infiltration preparation. Such a composition can be coated on articles that need to inhibit viruses, such as, but not limited to, masks, tissues, gloves, clothing, such as protective clothing. Alternatively, it can be added as an active ingredient to hand washing supplies, such as hand sanitizer, shower gel and the like. Such polypeptides or polypeptide derivatives can be used to inhibit coronavirus in vitro to prevent and/or reduce viral infections. Such polypeptides or polypeptide derivatives can be used to prevent or treat coronavirus infections or diseases caused by coronaviruses in subjects.

The polypeptides or polypeptide derivatives of the present invention can also be formulated into medicines or pharmaceutical compositions. Such medicine can be tablet, capsule, dripping pill, aerosol, pill, powder, solution, suspension, emulsion, granule, liposome, transdermal agent, suppository or lyophilized powder injection. These medicines or pharmaceutical compositions can be applied by various administration methods, such as injection, including subcutaneous injection, intravenous injection, intramuscular injection and intraperitoneal injection, intracisternal injection or infusion, etc., cavity administration, such as rectal, vaginal and sublingual, respiratory administration, such as through the nasal cavity; mucosal administration, or topical administration, etc.

The present invention provides a method for preventing or treating a coronavirus infection or a disease caused by a coronavirus in a subject, which comprises administering the polypeptide or polypeptide derivative of the present invention. The present invention also provides polypeptides or polypeptide derivatives for use in preventing or treating a coronavirus infection or a disease caused by a coronavirus in a subject.

The present invention also relates to a method for preventing or treating a coronavirus infection or a disease caused by a coronavirus in a subject, which comprises administering to the subject/patient the polypeptide, fusion protein or conjugate, nucleic acid, vector, host cell, polypeptide or polypeptide derivative or composition, Preferably, the coronavirus is 2019-nCoV, Rs3367-CoV or WIV1-CoV.

The present invention also relates to a polypeptide, a fusion protein or conjugate, a nucleic acid, a vector, a host cell, a polypeptide or a polypeptide derivative or a composition for use in preventing or treating a coronavirus infection or a disease caused by a coronavirus in a subject, preferably wherein the coronavirus is 2019-nCoV, Rs3367-CoV or WIV1-CoV.

The present invention also relates to a polypeptide, a fusion protein or conjugate, a nucleic acid, a vector, a host cell, a polypeptide or a polypeptide derivative or a composition, a pharmaceutical composition, and a kit for preventing or treating a coronavirus infection or a disease caused by a coronavirus in a subject/patient, preferably wherein the coronavirus is 2019-nCoV, Rs3367-CoV or WIV1-CoV.

EXAMPLES

The present invention is further illustrated by the following examples, but any examples or combinations thereof should not be construed as limiting the scope or implementation of the present invention. The scope of the present invention is defined by the appended claims. In combination with this specification and common knowledge in the field, a person of ordinary skill in the art can clearly understand the scope defined by the claims. Without departing from the spirit and scope of the present invention, those skilled in the art can make any modifications or changes to the technical solutions of the present invention, and such modifications and changes are also included in the scope of the present invention.

Experimental Materials:

Polypeptides:

The inventors designed three artificial polypeptides derived from the HR2 region by comparing the homology of the HR1 and HR2 sequences in the human coronavirus spike protein. The polypeptides simply referred to as a series of 2019-HR2P polypeptides (2019-HR2P, EK1-Plam and EK1-chol). The specific sequences and structures of these polypeptides are shown in Table 1. They are synthesized and purified by Shanghai SynPeptide Co Ltd, with purity of >95%.

TABLE 4

Specific sequences of the polypeptides used in the experiments:

| Name of polypeptide | Sequence of polypeptide |
|---|---|
| 2019-HR2P: | DISGINASVVNIQKEIDRLNEVAKNLNESLID LQEL (SEQ ID NO. 1) |
| EK1 | SLDQINVTFLDLEYEMKKLEEAIKKLEESYID LKEL (SEQ ID NO. 2) |
| EK1-plam | SLDQINVTFLDLEYEMKKLEEAIKKLEESYID LKEL-GSG-DPEG4-K(palmitic) |
| EK1-chol | SLDQINVTFLDLEYEMKKLEEAIKKLEESYID LKEL-GSGSG-DPEG4-C(cholesterol) |
| 2019-HR1P | ANQFNSAIGKIQDSLSSTASALGKLQDVVNQN AQALNTLVKQ (SEQ ID NO. 3) |

The amino acid sequence of 2019-nCoV-S in pAAV-IRES-EGFP-2019-nCoV-S (the restriction sites for insertion are BamHI and XhoI) is as follows:

(SEQ ID NO. 4)

MPMGSLQPLATLYLLGMLVASVLAQCVNLTTRTQLPPAYTNSFTRGV

YYPDKVFRSSVLHSTQDLFLPFFSNVTWFHAIHVSGTNGTKRFDNPV

LPFNDGVYFASTEKSNIIRGWIFGTTLDSKTQSLLIVNNATNVVIKV

CEFQFCNDPFLGVYYHKNNKSWMESEFRVYSSANNCTFEYVSQPFLM

DLEGKQGNFKNLREFVFKNIDGYFKIYSKHTPINLVRDLPQGFSALE

PLVDLPIGINITRFQTLLALHRSYLTPGDSSSGWTAGAAAYYVGYLQ

PRTFLLKYNENGTITDAVDCALDPLSETKCTLKSFTVEKGIYQTSNF

RVQPTESIVRFPNITNLCPFGEVFNATRFASVYAWNRKRISNCVADY

SVLYNSASFSTFKCYGVSPTKLNDLCFTNVYADSFVIRGDEVRQIAP

GQTGKIADYNYKLPDDFTGCVIAWNSNNLDSKVGGNYNYLYRLFRKS

NLKPFERDISTEIYQAGSTPCNGVEGFNCYFPLQSYGFQPTNGVGYQ

PYRVVVLSFELLHAPATVCGPKKSTNLVKNKCVNFNFNGLTGTGVLT

ESNKKFLPFQQFGRDIADTTDAVRDPQTLEILDITPCSFGGVSVITP

GTNTSNQVAVLYQDVNCTEVPVAIHADQLTPTWRVYSTGSNVFQTRA

GCLIGAEHVNNSYECDIPIGAGICASYQTQTNSPRRARSVASQSIIA

YTMSLGAENSVAYSNNSIAIPTNFTISVTTEILPVSMTKTSVDCTMY

ICGDSTECSNLLLQYGSFCTQLNRALTGIAVEQDKNTQEVFAQVKQI

YKTPPIKDFGGFNFSQILPDPSKPSKRSFIEDLLFNKVTLADAGFIK

QYGDCLGDIAARDLICAQKFNGLTVLPPLLTDEMIAQYTSALLAGTI

TSGWTFGAGAALQIPFAMQMAYRFNGIGVTQNVLYENQKLIANQFNS

AIGKIQDSLSSTASALGKLQDVVNQNAQALNTLVKQLSSNFGAISSV

LNDILSRLDKVEAEVQIDRLITGRLQSLQTYVTQQLIRAAEIRASAN

LAATKMSECVLGQSKRVDFCGKGYHLMSFPQSAPHGVVFLHVTYVPA

QEKNFTTAPAICHDGKAHFPREGVFVSNGTHWFVTQRNFYEPQIITT

DNTFVSGNCDVVIGIVNNTVYDPLQPELDSFKEELDKYFKNHTSPDV

DLGDISGINASVVNIQKEIDRLNEVAKNLNESLIDLQELGKYEQYIK

-continued

WPWYIWLGFIAGLIAIVMVTIMLCCMTSCCSCLKGCCSCGSCCKFDE

DDSEPVLKGVKLHYTGGTETSQVAPA.

The nucleotide sequence is as follows:

(SEQ ID NO. 5)

GGATCCGCCACCATGCCCATGGGGTCTCTGCAACCGCTGGCCACCTT

GTACCTGCTGGGGATGCTGGTCGCTTCCGTGCTAGCCCAGTGCGTGA

ACCTGACCACAAGGACCCAGCTGCCCCCTGCCTATACCAATTCCTTC

ACACGGGGCGTGTACTATCCCGACAAGGTGTTTAGAAGCTCCGTGCT

GCACTCTACACAGGATCTGTTTCTGCCTTTCTTTAGCAACGTGACCT

GGTTCCACGCCATCCACGTGAGCGGCACCAATGGCACAAAGCGGTTC

GACAATCCAGTGCTGCCCTTTAACGATGGCGTGTACTTCGCCTCTAC

CGAGAAGAGCAACATCATCAGAGGCTGGATCTTTGGCACCACACTGG

ACTCCAAGACACAGTCTCTGCTGATCGTGAACAATGCCACCAACGTC

GTGATCAAGGTGTGCGAGTTCCAGTTTTGTAATGATCCTTTCCTGGG

CGTGTACTATCACAAGAACAATAAGAGCTGGATGGAGTCCGAGTTTC

GCGTGTATTCTAGCGCCAACAATTGCACATTTGAGTACGTGTCCCAG

CCATTCCTGATGGACCTGGAGGGCAAGCAGGGCAATTTCAAGAACCT

GAGGGAGTTCGTGTTTAAGAATATCGATGGCTACTTCAAGATCTACT

CTAAGCACACCCCAATCAACCTGGTGCGCGACCTGCCACAGGGCTTC

AGCGCCCTGGAGCCACTGGTGGATCTGCCCATCGGCATCAACATCAC

CCGGTTTCAGACACTGCTGGCCCTGCACAGAAGCTACCTGACACCTG

GCGACTCCTCTAGCGGATGGACCGCAGGAGCTGCCGCCTACTATGTG

GGCTATCTGCAGCCAAGGACCTTCCTGCTGAAGTACAACGAGAATGG

CACCATCACAGACGCAGTGGATTGCGCACTGGACCCCCTGAGCGAGA

CCAAGTGTACACTGAAGTCCTTTACCGTGGAGAAGGGCATCTATCAG

ACATCCAATTTCAGGGTGCAGCCCACCGAGTCTATCGTGCGCTTTCC

CAATATCACAAACCTGTGCCCTTTTGGCGAGGTGTTCAACGCAACCA

GGTTCGCAAGCGTGTACGCATGGAATAGGAAGCGGATCAGCAACTGC

GTGGCCGACTATAGCGTGCTGTACAACTCCGCCTCTTTCAGCACCTT

TAAGTGCTATGGCGTGTCCCCCACAAAGCTGAATGACCTGTGCTTTA

CCAACGTGTACGCCGATTCTTTCGTGATCAGGGGCGACGAGGTGCGC

CAGATCGCACCAGGACAGACAGGCAAGATCGCAGACTACAATTATAA

GCTGCCTGACGATTTCACCGGCTGCGTGATCGCCTGGAACAGCAACA

ATCTGGATTCCAAAGTGGGCGGCAACTACAATTATCTGTACCGGCTG

TTTAGAAAGTCTAATCTGAAGCCATTCGAGAGGGACATCTCTACAGA

GATCTACCAGGCAGGCAGCACCCCATGCAATGGAGTGGAGGGCTTTA

ACTGTTATTTCCCTCTGCAGAGCTACGGCTTCCAGCCAACAAACGGC

GTGGGCTATCAGCCCTACCGCGTGGTGGTGCTGAGCTTTGAGCTGCT

GCACGCACCTGCAACAGTGTGCGGACCAAAGAAGTCCACCAATCTGG

TGAAGAACAAGTGCGTGAACTTCAACTTCAACGGACTGACCGGCACA

-continued

GGCGTGCTGACCGAGTCCAACAAGAAGTTCCTGCCCTTTCAGCAGTT

CGGCAGGGACATCGCAGATACCACAGACGCCGTGCGCGACCCTCAGA

CCCTGGAGATCCTGGACATCACACCATGCTCTTTCGGCGGCGTGAGC

GTGATCACACCTGGCACCAATACAAGCAACCAGGTGGCCGTGCTGTA

TCAGGACGTGAATTGTACCGAGGTGCCCGTGGCAATCCACGCAGATC

AGCTGACCCCTACATGGCGGGTGTACAGCACCGGCTCCAACGTGTTC

CAGACAAGAGCCGGATGCCTGATCGGAGCAGAGCACGTGAACAATTC

CTATGAGTGCGACATCCCTATCGGCGCCGGCATCTGTGCCTCTTACC

AGACCCAGACAAACTCTCCAAGGAGAGCCCGGAGCGTGGCATCCCAG

TCTATCATCGCCTATACAATGAGCCTGGGCGCCGAGAACAGCGTGGC

CTACTCTAACAATAGCATCGCCATCCCTACCAACTTCACAATCTCCG

TGACCACAGAGATCCTGCCAGTGTCCATGACCAAGACATCTGTGGAC

TGCACAATGTATATCTGTGGCGATTCTACCGAGTGCAGCAACCTGCT

GCTGCAGTACGGCAGCTTTTGTACCCAGCTGAATAGAGCCCTGACAG

GCATCGCCGTGGAGCAGGACAAGAACACACAGGAGGTGTTCGCCCAG

GTGAAGCAGATCTACAAGACCCCACCCATCAAGGACTTTGGCGGCTT

CAATTTTTCCCAGATCCTGCCCGATCCTTCCAAGCCTTCTAAGCGGA

GCTTTATCGAGGACCTGCTGTTCAACAAGGTGACCCTGGCCGATGCC

GGCTTCATCAAGCAGTATGGCGATTGCCTGGGCGACATCGCCGCCAG

AGACCTGATCTGTGCCCAGAAGTTTAATGGCCTGACCGTGCTGCCTC

CACTGCTGACAGATGAGATGATCGCACAGTACACAAGCGCCCTGCTG

GCAGGCACCATCACATCCGGATGGACCTTCGGCGCAGGAGCCGCCCT

GCAGATCCCCTTCGCTATGCAGATGGCCTATCGGTTCAACGGCATCG

GCGTGACCCAGAATGTGCTGTACGAGAACCAGAAGCTGATCGCCAAT

CAGTTTAACTCCGCCATCGGCAAGATCCAGGACAGCCTGTCCTCTAC

AGCCTCCGCCCTGGGCAAGCTGCAGGATGTGGTGAATCAGAACGCCC

AGGCCCTGAATACCCTGGTGAAGCAGCTGAGCTCCAACTTCGGCGCC

ATCTCTAGCGTGCTGAATGACATCCTGAGCCGGCTGGACAAGGTGGA

GGCAGAGGTGCAGATCGACCGGCTGATCACAGGCAGACTGCAGTCTC

TGCAGACCTACGTGACACAGCAGCTGATCAGGGCAGCAGAGATCAGG

GCAAGCGCCAATCTGGCAGCAACCAAGATGTCCGAGTGCGTGCTGGG

CCAGTCTAAGAGAGTGGACTTTTGTGGCAAGGGCTATCACCTGATGT

CCTTCCCACAGTCTGCCCCTCACGGAGTGGTGTTTCTGCACGTGACC

TACGTGCCAGCCCAGGAGAAGAACTTCACCACAGCACCAGCAATCTG

CCACGATGGCAAGGCACACTTTCCCAGGGAGGGCGTGTTCGTGAGCA

ACGGCACCCACTGGTTTGTGACACAGCGCAATTTCTACGAGCCTCAG

ATCATCACCACAGACAATACATTCGTGTCCGGCAACTGTGACGTGGT

CATCGGCATCGTGAACAATACCGTGTATGATCCTCTGCAGCCAGAGC

TGGACAGCTTTAAGGAGGAGCTGGATAAGTACTTCAAGAATCACACC

TCCCCAGACGTGGATCTGGGCGACATCAGCGGCATCAATGCCTCCGT

-continued

GGTGAACATCCAGAAGGAGATCGACAGGCTGAACGAGGTGGCCAAGA

ATCTGAACGAGAGCCTGATCGATCTGCAGGAGCTGGGCAAGTATGAG

CAGTACATCAAGTGGCCCTGGTATATCTGGCTGGGCTTCATCGCCGG

CCTGATCGCTATCGTGATGGTGACCATCATGCTGTGCTGTATGACAT

CCTGCTGTTCTTGCCTGAAGGGCTGCTGTAGCTGTGGCTCCTGCTGT

AAGTTTGATGAGGACGATTCCGAGCCAGTGCTGAAGGGCGTGAAGCT

GCACTACACCGGCGGCACCGAGACATCTCAGGTGGCCCCCGCCTAAC

TCGAG

Figure 8A:
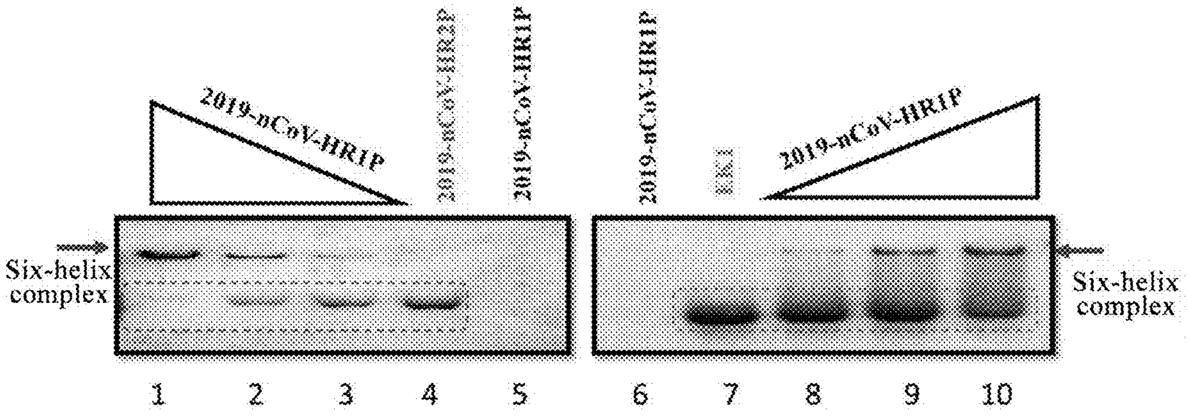
FIGS. 8*a*-8*b*: 2019-HR2P represents the antiviral mechanism of the polypeptide.

The plasmid map of pAAV-IRES-EGFP is shown in FIG. 8. pAAV-IRES-EGFP was purchased from Agilent technologies in the United States. pcDNA3.1-SARS-CoV-S plasmid, pcDNA3.1-Rs3367-CoV-S plasmid, pcDNA3.1-WIV1-CoV-S plasmid and pNL4-3.luc.RE plasmid were kindly donated by Dr. Du Lanying from the New York Blood Center, USA. The restriction sites for inserting 2019-nCoV-S into pcDNA3.1 are BamHI and XhoI.

The target cell HuH7 cell expressing the receptor of human coronavirus infection: purchased from the cell bank of the Chinese Academy of Sciences

Example 1: Preparation of 2019-nCoV or SARS-CoV or Rs3367-CoV or WIV1-CoV Pseudovirus Experimental Method:

1. 293T cells were digested 24 hours before transfection and were plated in a 10 cm tissue culture dish ($2\times10^6$/dish).
2. The culture medium was replaced with fresh pre-warmed DMEM medium (containing 10% FBS) 2 hours before transfection.
3. Two 1.5 mL EP tubes were used for transfection. 500 μL 0.9% NaCl solution was added to EP tube 1, which contained 20 μg of pcDNA3.1-plasmid (or pcDNA3.1-SARS-CoV-S plasmid or pcDNA3.1-Rs3367-CoV-S plasmid or pcDNA3.1-WIV1-CoV-S plasmid) and pNL4-3.luc.RE plasmid each (these plasmids were kindly provided by Dr. Du Lanying from the New York Blood Center, USA. The relevant information can also be found in the literature, Xia, S.[#], Yan, L.[#], Xu, W.[#], Agrawal, A. S., Alsaissi, A., Tseng, C. T. K., Wang, Q., Du, L., Tan, W., Wilson, I. A.*, Jiang, S.*, Yang, B.*, Lu, L.* (2019). A pan-coronavirus Fusion Inhibitor Targeting the HR1 Domain of Human Coronavirus Spike. *Science Advances.* 2019 Apr. 10; 5(4): eaav4580). 500 μL 0.9% NaCl was also added to EP tube 2, and then 10 μL of transfection reagent vigofect was added. Both of the tubes were stood for 5 minutes.
4. 500 μL of the solution in EP tube 2 was added to EP tube 1 dropwise, mixed well with a pipette tip while being added, and left at room temperature for 15 minutes.
5. 1 mL of mixed liquid obtained above was added dropwise and evenly to the 293T cell previously plated in culture dish.
6. After 8-10 hours of culture, the culture medium was replaced with 10 mL of fresh DMEM culture medium containing 10% FBS.
7. The supernatant containing pseudovirus was collected into the tubes after 48 hours;

8. The tubes were centrifuged at 4000 rpm for 4 mins to remove cell debris, filtered with a 0.45 μm sterile filter, aliquoted and stored at −80° C. for later use.

Example 2: Inhibition of Human Coronavirus S Protein-Mediated Cell-Cell Fusion

Experimental Method:

1. 293T cells were transfected with the plasmid encoding the human coronavirus S protein and are cultured for 36-48 hours to be served as effector cells. Specifically, 293T cells were transfected with the plasmid pAAV-IRES-GFP-2019-nCoV-S encoding the 2019-nCoV S protein to obtain transfected cells, which are referred as 293T/2019/EGFP cells. 293T cells were transfected with the empty vector plasmid pAAV-IRES-GFP to obtain 293T/EGFP cells, which were used as negative control cells.
2. 293T/2019/EGFP cells and 293T/EGFP cells were digested with 0.02% EDTA, centrifuged, and resuspended in fresh DMEM medium containing 10% FBS to adjust cell concentration to $2\times10^5$ cells/mL. 50 μL of 293T/2019/EGFP cells or 293T/EGFP cells was added into various test polypeptide drugs (50 μL) in serial dilutions, and incubated at 37° C. for 30 min. Those without drugs were used as positive control cells.
3. 100 μL of the cell/drug mixture was added to the target cells (Huh-7) that had been plated on a 96-well plate, which was incubated in 5% CO2 at 37° C. for 2-4 hours. The fusion status of the target cells was observed with the fluorescence microscope and recorded.

Calculation formula for inhibitory activity is: Inhibition rate=(number of fused cells in positive wells−number of fusion in drug wells)/(number of fused cells in positive wells−number of fusion in negative wells)*100.

Figure 2:
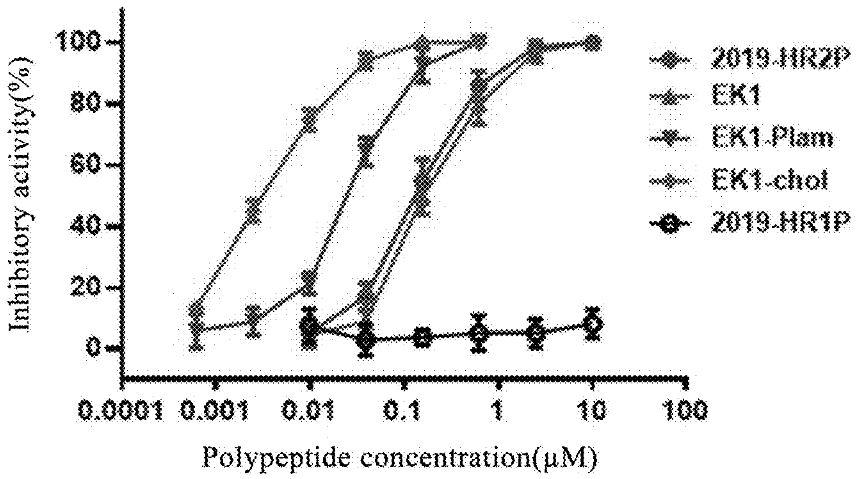
FIG. 2: Inhibitory activity of the polypeptide on cell-cell fusion mediated by the S protein of 2019-nCoV.

Results and Discussion:

As shown in FIG. 2, the series of 2019-HR2P polypeptides, 2019-HR2P, EK1-Plam, EK1-chol and EK1 have a very good inhibitory effect on the cell-cell fusion mediated by the S protein of 2019-nCoV. The results preliminarily show that the series of 2019-HR2P polypeptides can inhibit 2019-nCoV. For the cell-cell fusion mediated by the S protein of 2019-nCoV, compared with EK1, the inhibitory activity of its derivatives EK1-Plam and EK1-chol is significantly enhanced, and the polypeptide 2019-HR2P has considerable inhibitory activity.

Example 3: Determination of the Inhibitory Activity of Polypeptides Against 2019-nCoV and Other Coronavirus Pseudoviruses Experimental Method:

1. The test polypeptide was dissolved using DMSO and the polypeptide concentration was determined.
2. Cell suspension of target cells (HuH7 expressing the human infectious coronavirus receptor) was prepared, and adjusted the cell concentration in each well to $10^4$ cells.
3. The polypeptide drug was diluted in a 2-fold gradient using DMEM culture medium containing 10% FBS, with 50 μL per well.
4. A certain titer of 2019-nCoV or SARS-CoV or Rs3367-CoV or WIV1-CoV pseudovirus was added to the plate with the drug dilutions at 50 μL/well, which was then incubated at room temperature for 30 mins to allow the drug and virus fully interact. 100 μL of the drug and virus mixture was added to the target cells in each well from which the supernatant has been removed. After incubation for 12 hours at 37° C., they were replaced with fresh DMEM medium containing 10% FBS.
5. Luciferase activity was measured after 72 hours, the inhibition rate curve was produced. The half inhibitory concentration (IC50) of the drug was calculated.

Calculation formula for inhibitory activity: Inhibition rate=(value of virus control well−value of drug well)/(value of virus control well−value of cell well)*100%. The virus control well is the well without drug, and the cell well is the well without virus.

Results and Discussion:

The antiviral activity of the series of 2019-HR2P polypeptides was tested on 2019-nCoV or SARS-CoV or Rs3367-CoV or WIV1-CoV pseudovirus system. The results are shown in FIGS. 3-6 and Table 5. The 2019-HR2P, EK1-Plam, EK1-chol and EK1 polypeptides also exhibited potent antiviral activity, which was consistent with the results of previous cell-cell fusion experiments. In addition, the inhibitory activity of EK1-Plam and EK1-chol polypeptides was significantly better than that of EK1 polypeptides, up to about tens of times.

TABLE 5

The inhibitory activity of the series of 2019-HR2P polypeptides on a variety of human coronavirus pseudoviruses:

| Name of polypeptide | Inhibitory Activity, IC50(μM) | | | |
|---|---|---|---|---|
| | 2019n-CoV | SARS-CoV | Rs3367 | WIV1-CoV |
| 2019-nCoV-HR2P | 1.05 | 3.75 | 5.05 | 4.24 |
| EK1 | 2.49 | 1.89 | 4.00 | 2.94 |
| EK1-plam | 0.36 | 0.17 | 0.13 | 0.10 |
| EK1-chol | 0.02 | 0.01 | 0.03 | 0.04 |

Example 4: Determination of the Inhibitory Activity of Polypeptides Against Live 2019-nCoV Virus Infection Experimental Method:

This study was authorized to be performed by the biosafety level 3 laboratory of Wuhan Institute of Virology, Chinese Academy of Sciences. In particular, the inhibitory activity of 2019-HR2P, EK1-Plam, EK1-chol and EK1 against the 2019-nCoV live virus was detected by the plaque reduction assay. The different concentrations of polypeptides as described above were first incubated with the live 2019-nCoV virus (virus titer of 100 PFU) for 30 minutes, and then they were added to the monolayer of VERO-E6 cells. After culturing at 37° C. for 1 hour, the culture supernatant was removed. Then 0.9% methylcellulose was added to cover the cells. After 72 hours, the cells were stained to observe and count the number of plaques. Calculation formula for Inhibition activity: inhibition rate=(number of plaques in virus control wells−number of plaques in drug wells)/number of plaques in virus control wells*100%.

Figure 7:
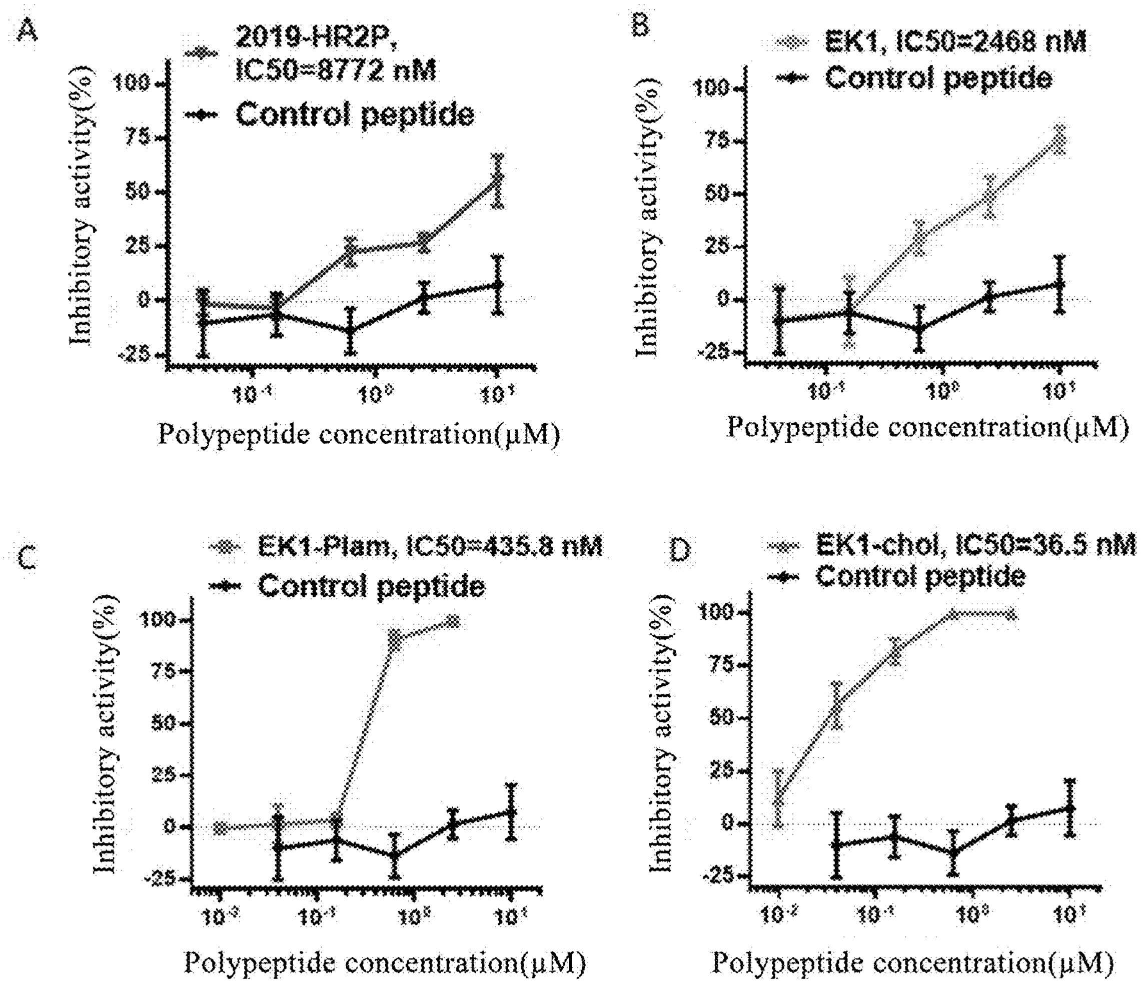
FIG. 7: Inhibitory activity of the polypeptide on the live 2019-nCoV virus.

Results and Discussion:

The antiviral activity of the series of 2019-HR2P polypeptides was detected on the 2019-nCoV live virus system. The results are shown in FIG. 7. The 2019-HR2P, EK1-Plam, EK1-chol and EK1 polypeptides all exhibited effective the 2019-nCoV live virus inhibitory activities, while the control peptide did not exhibit inhibitory activity. In addition, the inhibitory activity of EK1-Plam and EK1-chol polypeptides were significantly better than that of EK1 polypeptide, which was 5 times and 67 times higher, respectively. Specifically, on the 2019-nCoV live virus system, the IC50 of EK1 is 2468 nM, the IC50 of EK1-Plam is 435.8 nM, and the IC50 of EK1-chol is 36.5 nM.

Example 5: Study on the Antiviral Mechanism of the HR2 Polypeptide

Taking the 2019-HR2P polypeptide as an example and EK1 polypeptide as a control, the interaction between the polypeptides and the polypeptide 2019-HR1P, which is derived from the HR1 region of 2019-nCoV, is detected, so as to further explore the antiviral mechanism of the 2019-HR2P polypeptide.

Experimental Method:

1. Non-denaturing (Native) polyacrylamide gel electrophoresis (N-PAGE). The polypeptide 2019-HR1P belonging to the series of HR1 polypeptides was mixed with the polypeptide 2019-HR2P or EK1 belonging to the series of HR2 polypeptides (final concentration of 30 μM each), respectively, and was incubated at 37° C. for 30 minutes. 5× loading buffer at a high pH was mixed with 4 times the volume of the peptide mixture, which was then loaded (25 μl per well) in 18% non-denaturing gel (Tiandz, Beijing) to conduct electrophoresis at 125V constant voltage for 2 hours at room temperature, and was stained with Coomassie brilliant blue.
2. Determination of the secondary structure of the polypeptide by circular dichroism spectroscopy. The alone polypeptide or polypeptide mixture was diluted with 50 mmol/L phosphate buffer, pH 7.2 to a final concentration of 10 μmol/L. The circular dichroism spectra were measured using a spectropolarimeter (Model J-815, Jasco Inc, Japan). The detection temperature was 4° C., with 5.0 nm of bandwidth, 0.1 nm of resolution, 0.1 cm of optical path, 4.0 s of reaction time, and 50 nm/min of scanning speed. The thermal denaturation of the polypeptide was monitored at 222 nm with a temperature gradient of 5° C./min. The blank control of the buffer solution was subtracted to correct the spectrum value. The melting curve was smoothed, and the midpoint temperature of the thermal dissociation transition, i.e., the Tm value, was calculated with Jasco.

Results and Analysis:

1. After the 2019-HR2P is mixed with the 2019-HR1P polypeptide, a new band that may be a six-helix bundle complex is produced (FIG. 8*a*, legend: lanes 1, 2, and 3 are 2019-nCoV-HR1P+2019-nCoV-HR2P; lane 4 is 2019-nCoV-HR2P; lane 5 is 2019-nCoV-HR1P). EK1 also showed a similar effect, proving the stability of the system and the formation of a six-helix bundle complex by EK1 (FIG. 8*a*, legend: lane 6 is 2019-nCoV-HR1P; lane 7 is EK1; lanes 8, 9, 10 are EK1+2019-nCoV-HR1P).
2. A single polypeptide has a low helical structure. When the 2019-HR2P polypeptide is mixed with the 2019-HR1P polypeptide, a high helical structure appears. This result is consistent with the CD spectrum of the six-helix bundle (6-HB) structure. And its Tm value indicates its thermal stability. EK1 also showed a similar effect, proving the stability of the system and EK1 also formed a 6-HB complex.

Discussion

In summary, the present invention found for the first time that the series of 2019-HR2P polypeptides (2019-HR2P, EK1, EK1-Plam and EK1-chol) have a good inhibitory activity against 2019-nCoV, and the mechanism of action is to form a stable heterologous 6HB by binding to the HR1 region of the virus, preventing the interaction of the viral HR2 and HR1 trimers, preventing the formation of homologous 6HB, thereby interfering with the fusion between the virus and the cell membrane and blocking the virus infection. In addition, it was also found that the series of 2019-HR2P polypeptides (2019-HR2P, EK, EK1-Plam and EK1-chol) have a good inhibitory activity against SARS viruses and SARS-like viruses (Rs3367-CoV and WIV1-CoV). It was found for the first time that the activities of EK1-Plam and EK1-chol are significantly higher than that of EK1, up to tens of times.

In the present invention, the inventors detected the inhibitory activity of the series of 2019-HR2P polypeptides (2019-HR2P, EK1-Plam and EK1-chol) on the corresponding virus fusion process by establishing a cell-cell fusion system mediated by 2019-nCoV and SARS-like virus S protein, as shown in FIG. 2. In 2014, lu 1. (Lulu, one of the inventors of this patent) and others constructed a cell-cell fusion system for SARS-CoV, MERS-CoV, etc. by co-expressing the S protein of the virus and GFP, and successfully designed and evaluated a series of polypeptide entry inhibitors with better activity based on this well-recognized system for simulating virus infection. The results were published in Nature Communications and Science Advances. In the present invention, using the same method, the inventors took the lead in establishing a 2019-nCoV S protein-mediated membrane fusion system in the world, and separately detected the membrane fusion inhibitory effects of the series of polypeptides invented on 2019-nCoV and SARS-like viruses, with the polypeptide entry inhibitor EK1 having the best activity at present as a control (References: Lu, L., Q. Liu, Y. Zhu, K. H. Chan, L. Qin, Y. Li, Q. Wang, J. F. Chan, L. Du, F. Yu, C. Ma, S. Ye, K. Y. Yuen, R. Zhang, and S. Jiang. 2014. Structure-based discovery of Middle East respiratory syndrome coronavirus fusion inhibitor. Nat Commun 5:3067. and Xia, S., Yan, L., Xu, W., Agrawal, A. S., Alsaissi, A., Tseng, C. T. K., Wang, Q., Du, L., Tan, W., Wilson, I. A., Jiang, S., Yang, B., Lu, L. A pan-coronavirus Fusion Inhibitor Targeting the HR1 Domain of Human Coronavirus Spike. Science Advances. 2019 Apr. 10; 5(4):eaav4580). In the cell-cell fusion experiment of 2019-nCoV, all the series of 2019-HR2P polypeptides and EK1 polypeptides showed good inhibitory effects, and the inhibitory activity of EK1-Plam and EK1-chol polypeptides was significantly better than that of EK1 polypeptides, up to about 10-100 times (FIG. 2). The negative control 2019-HR1P polypeptide showed no activity.

Figure 3:
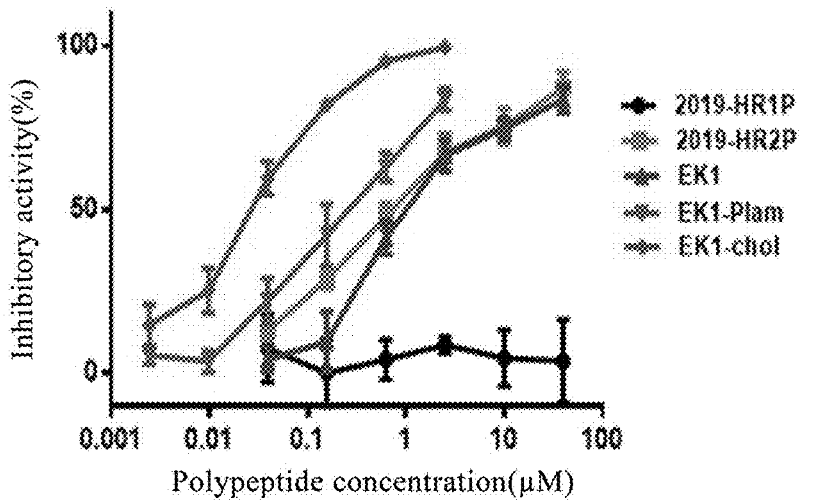
FIG. 3: Inhibitory activity of the polypeptide on the 2019-nCoV pseudovirus.
Figure 4:
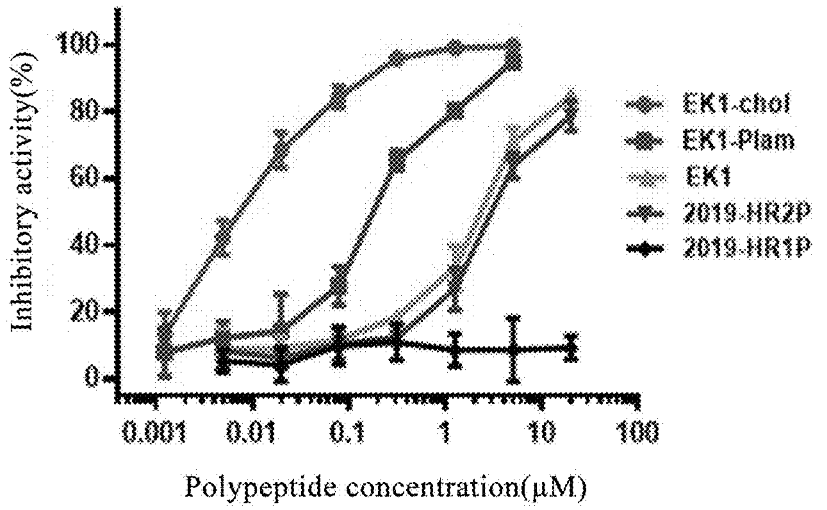
FIG. 4: Inhibitory activity of the polypeptide on the SARS-CoV pseudovirus.
Figure 5:
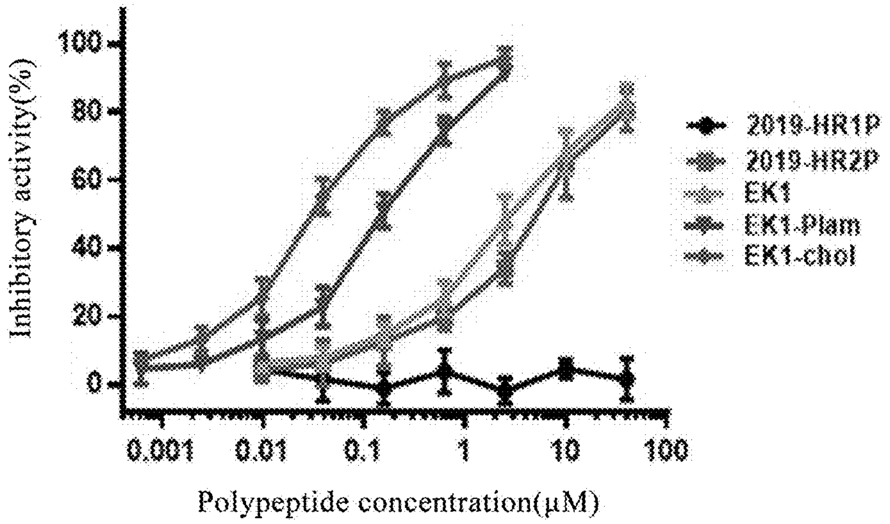
FIG. 5: Inhibitory activity of the polypeptide on the Rs3367-CoV pseudovirus.
Figure 6:
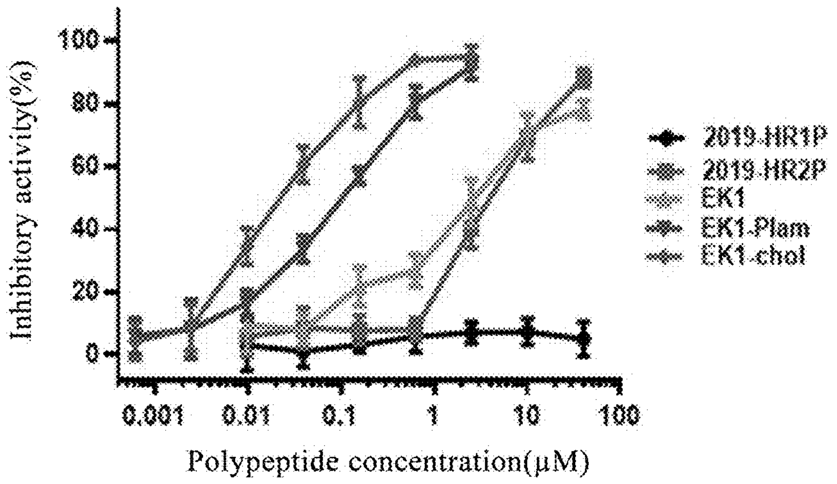
FIG. 6: Inhibitory activity of the polypeptide on the WIV1-CoV pseudovirus.

At the same time, in order to further determine the inhibitory activity of the polypeptide or polypeptide derivative of the present invention, the inventors also used another well-recognized model for evaluation of antiviral drug activity—pseudovirus infection model in the present invention. The inventors took the lead in establishing the 2019-nCoV pseudovirus infection system in the world, and then detected the inhibitory effect of the series of 2019-HR2P polypeptides and the control EK1 polypeptide on the pseudovirus. As shown in FIG. 3, the series of 2019-HR2P polypeptides showed good inhibitory effects on both 2019-nCoV pseudoviruses and live viruses, and the inhibitory activities of EK1-Plam and EK1-chol polypeptides were significantly better than that of EK1 polypeptides, up to approximately 6-120 times (FIG. 3 and Table 2). This result is consistent with the result of the MERS-CoV cell-cell fusion experiment as described above. Similar results were also obtained in the SARS virus and SARS-like pseudovirus inhibition experiments (FIGS. 4, 5, 6 and 7). The negative control 2019-HR1P polypeptide showed no activity.

Figure 8B:
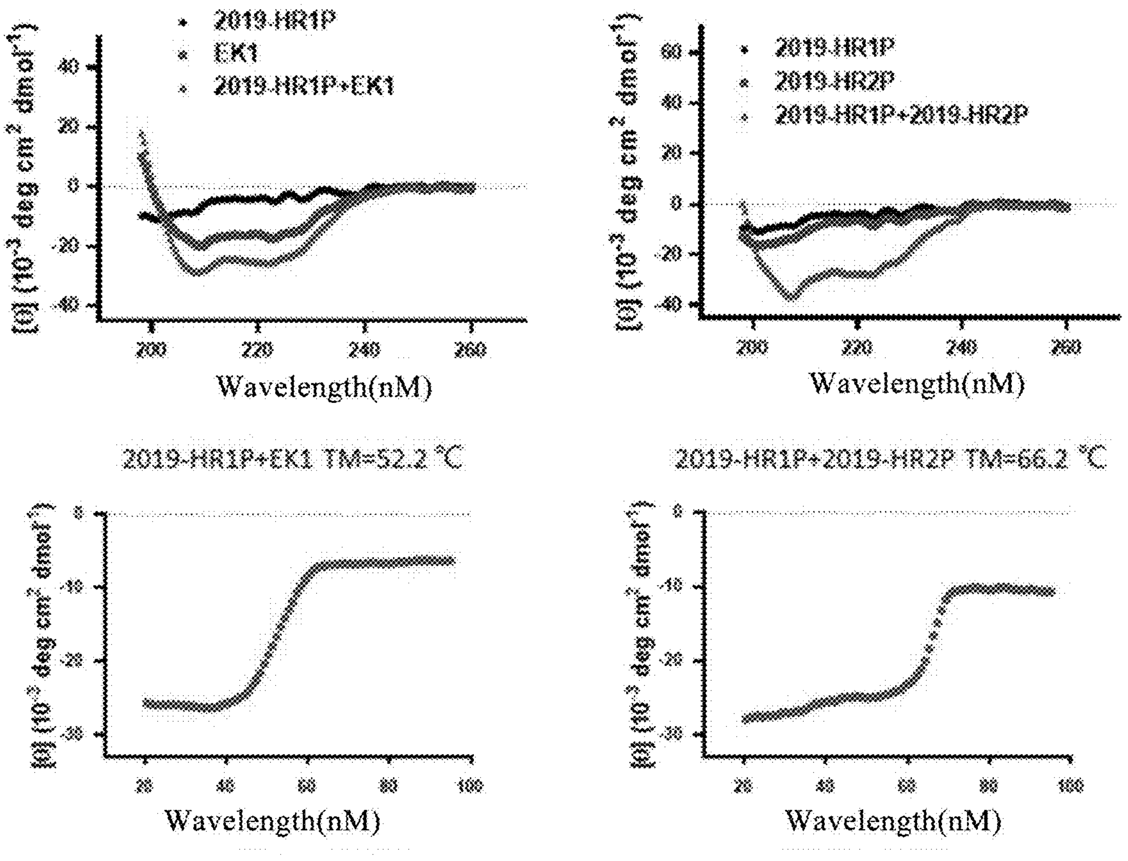
Figure 9:
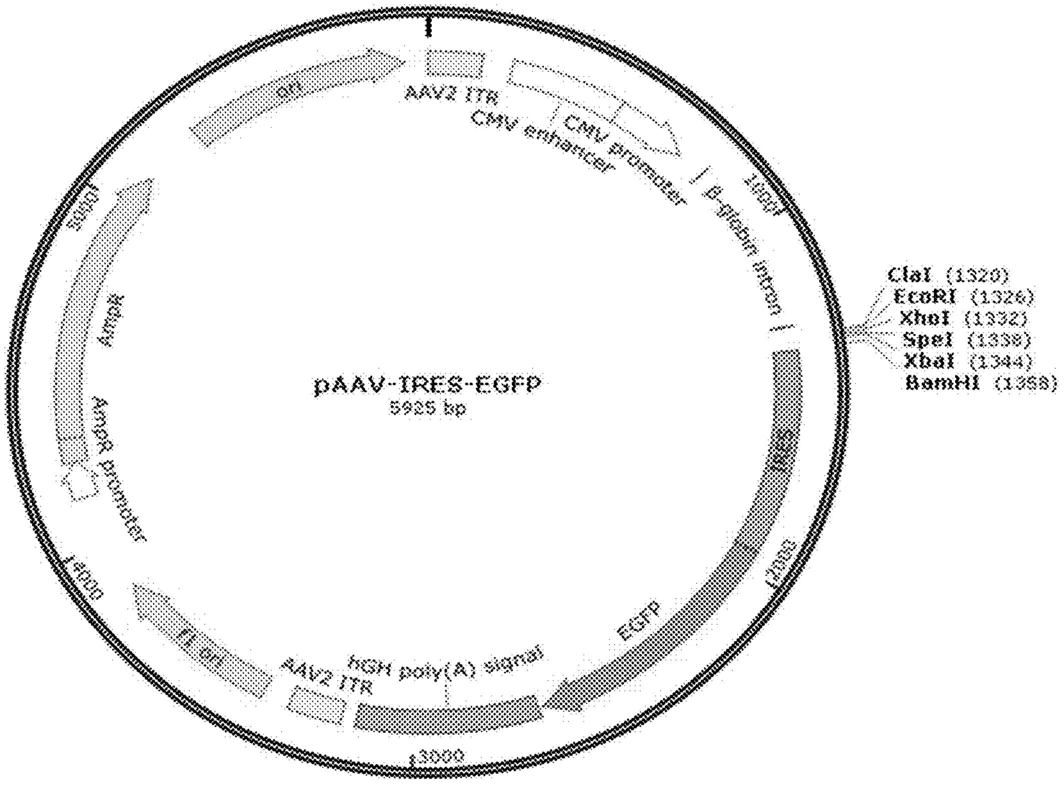
FIG. 9: pAAV-IRES-EGFP plasmid map.

The polypeptides or polypeptide derivatives of the present invention not only show a highly effective activity against 2019-nCoV, but also show their specific antiviral mechanism as exemplified by the 2019-HR2P polypeptide. In the Native PAGE experiment shown in FIG. 8*a*, the 2019-HR2P polypeptide and EK1 polypeptide can be mixed with the 2019-HR1P derived from the 2019-nCoV HR1 region, and both produce a new band, which is a six-helix band. In addition, the detection of the secondary structure of polypeptides showed that when the 2019-HR2P polypeptide and EK1 polypeptide were mixed with the 2019-HR1P, a high degree of helical structure appeared. This result was consistent with the CD spectrum of the six-helix core structure, and its Tm value indicated its thermal stability (FIG. 8*b*). It can be seen that the antiviral mechanism of the 2019-HR2P polypeptide is mainly through binding to the HR1 region of the 2019-nCoV virus to interfere with the viral 6HB formation, thereby inhibiting the fusion and entry processes of the virus.

In summary, the series of 2019-HR2P polypeptides have a good inhibitory activity against the 2019-nCoV, SARS viruses, and SARS-like viruses, providing a good preventive and therapeutic candidate drug for the currently circulating 2019-nCoV and the SARS-like viruses that may break out in the future. In addition, the clear antiviral mechanism of the 2019-HR2P polypeptide can ensure the safety of its application and the clarity of the optimization approach, which is convenient for further development in the future.

Example 6: Inhibition of the SARS-CoV-2 Live Virus by EK1 and EK1-Chol on the Human Intestinal Cell Line CaCO2

(I) Experimental Methods:

1. This experiment was carried out in the biosafety level 3 laboratory of Fudan University, and the SARS-CoV-2 strain used was the nCoV-SHO1 strain isolated in this laboratory.
2. CaCO2 cells were plated in a 96-well plate (10,000 cells per well) 12 hours before infection.
3. The polypeptide inhibitor was serially diluted using the serum-free DMEM with the volume of 50 μL, and 50 μL of virus diluent (750 pfu/ml) was then added, and mixed, followed by incubation at 37° C. for 30 mins.
4. 100 μL of virus/drug mixture was added to the target cells that had been plated in a 96-well plate, and incubated with 5% CO2 at 37° C. for 48 hours.
5. The supernatant of each well was collected and quantitatively detected for the amount of viral RNA in the supernatant to calculate the inhibition rate.

Figure 10:
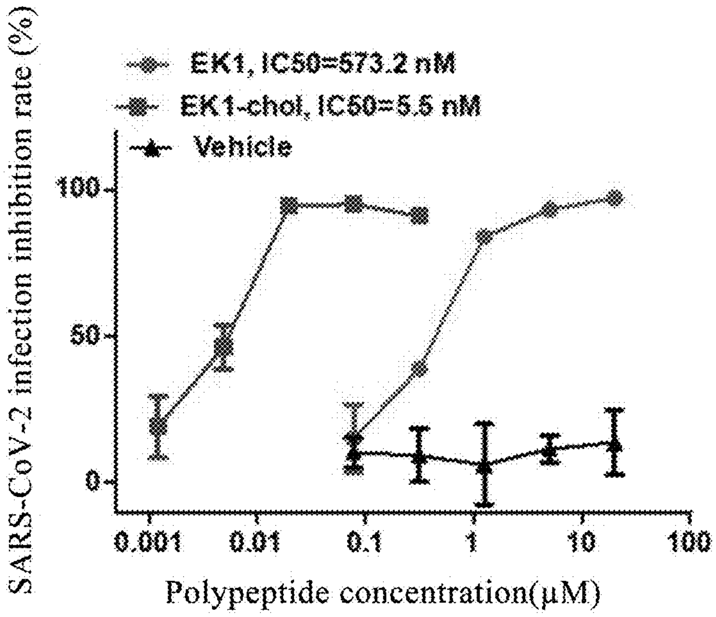
FIG. 10: Inhibitory effect of polypeptides EK1 and EK1-chol on infection of the SARS-CoV-2 live virus.

The results show that:

SARS-CoV-2 can effectively infect human intestinal tissues, so it is of great significance for us to use human intestinal cell lines to evaluate the polypeptides EK1 and EK1-chol. The results are shown in FIG. 10 that both EK1 and EK1-chol polypeptides have highly effective inhibitory effects on SARS-CoV-2, and their half inhibitory concentrations are 573.2 nM and 5.5 nM, respectively.

Example 7: In Vivo Protective Effect of the Polypeptide EK1 on Transgenic Mice Infected with the SARS-CoV-2 Live Virus (I) Experimental Methods:

1. This experiment was carried out in the biosafety level 3 laboratory of Fudan University, and the SARS-CoV-2 strain used was the nCoV-SH01 strain isolated in this laboratory; the transgenic human-ACE2 mice were purchased from Shanghai Model Organisms Center, Inc.; Mouse strain: Tgtn (CAG-human ACE2-IRES-Luciferase).
2. Each mouse was challenged with 30,000 pfu SARS-CoV-2 (30 μL).
3. 30 minutes before the challenge; or 30 minutes after the challenge, the dose of 200 μg EK1/mouse was administered by intranasal route.
4. The mice were euthanized on the 4th day after infection, and the viral load of the lungs and intestinal tissues of mice in each group was detected.

Figure 11:
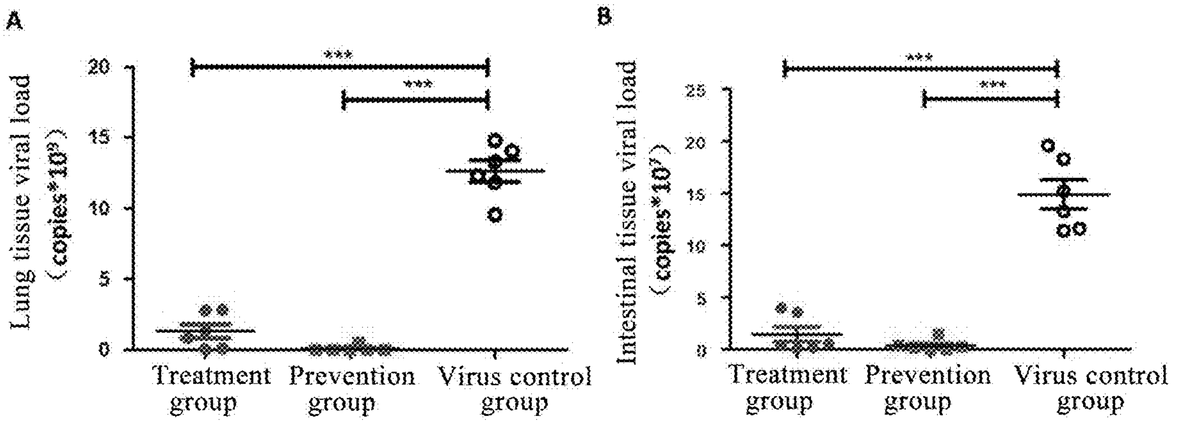
FIG. 11: Preventive and therapeutic protective effects of EK1 polypeptide in vivo. A. changes in lung viral load; B. changes in enteric viral load.

(II) the Results Show that:

The therapeutic administration of the EK1 polypeptide through the respiratory tract by nose drops can significantly reduce the SARS-CoV-2 viral load in the lung (A) and intestine (B) (FIG. 11), indicating that EK1 has a better protective effect in vivo.

Example 8: In Vivo Protective Effect of the Polypeptide EK1-Chol on Transgenic Mice Infected with the SARS-CoV-2 Live Virus (I) Experimental Methods:

1. This experiment was carried out in the biosafety level 3 laboratory of Fudan University, and the SARS-CoV-2 strain used was the nCoV-SH01 strain isolated in this laboratory; the transgenic human-ACE2 mice were purchased from Shanghai Model Organisms Center, Inc.; Mouse strain: Tgtn (CAG-human ACE2-IRES-Luciferase).
2. Each mouse was challenged with 30,000 pfu SARS-CoV-2 (30 μL).
3. 30 minutes before the challenge; or 30 minutes after the challenge, the dose of 10 μg EK1C4/mouse was administered by intranasal route.
4. On the 4th day after infection, the mice were euthanized, and the viral load of the lungs and intestinal tissues of mice in each group was detected.

Figure 12:
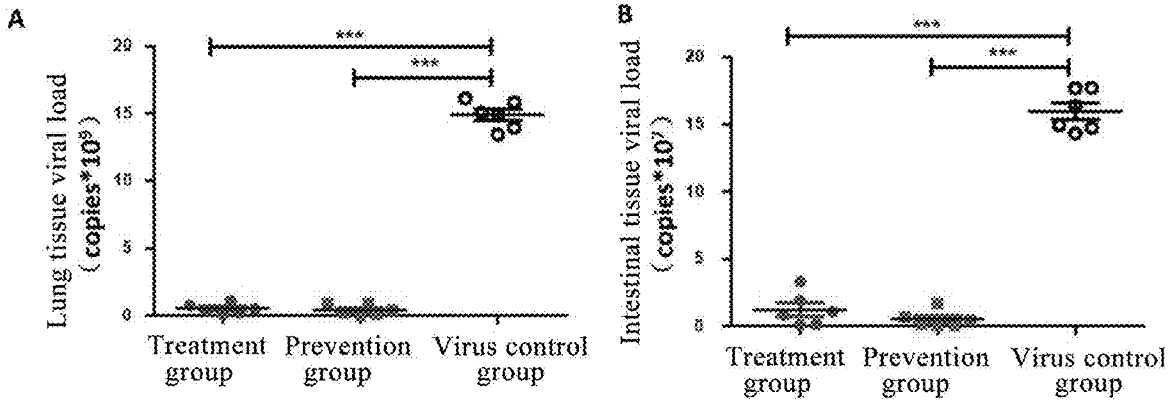
FIG. 12: Preventive and therapeutic protective effects of EK1-chol polypeptide in vivo. A. changes in lung viral load; B. changes in enteric viral load.

(II) the Results Show that:

The therapeutic administration of the EK1-chol polypeptide through the respiratory tract by nose drops can significantly reduce the SARS-CoV-2 viral titer in the lung (A) and intestine (B) (FIG. 12), indicating that EK1-chol has an effectively protective effect in vivo.

The invention claimed is:

1. A polypeptide derivative having a sequence of SLDQ-INVTFLDLEYEMKKLEEAIKKLEESYIDLKEL-(GSGSG)n-PEG4-C-cholesterol as set forth in SEQ ID NO. 14, wherein n is 1.

2. A composition comprising the polypeptide derivative in claim 1.

3. The composition of claim 2, wherein the composition is an external preparation.

4. A method for inhibiting a coronavirus, or treating a coronavirus infection in a subject, comprising administering the polypeptide derivative in claim 1 to the subject.

5. The method of claim 4, wherein the coronavirus is 2019-nCoV, Rs3367-CoV or WIV1-CoV.

6. The method of claim 4, wherein said disease is coronavirus pneumonia.

7. The method of claim 4, wherein further administering an agent for inhibiting the coronavirus or treating the coronavirus infection.

* * * * *